US009110042B2

(12) United States Patent
Nakaya et al.

(10) Patent No.: US 9,110,042 B2
(45) Date of Patent: Aug. 18, 2015

(54) CLINICAL SPECIMEN PROCESSING APPARATUS AND CLINICAL SPECIMEN PROCESSING SYSTEM

(75) Inventors: Masanori Nakaya, Kobe (JP); Hideyuki Higuchi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 104 days.

(21) Appl. No.: 12/829,919

(22) Filed: Jul. 2, 2010

(65) Prior Publication Data

US 2010/0290950 A1   Nov. 18, 2010

Related U.S. Application Data

(63) Continuation of application No. 11/155,439, filed on Jun. 17, 2005, now Pat. No. 7,776,271.

(30) Foreign Application Priority Data

Jun. 17, 2004 (JP) .................. 2004-179051

(51) Int. Cl.
*G01N 35/02* (2006.01)
*G01N 35/10* (2006.01)
*G01N 35/00* (2006.01)

(52) U.S. Cl.
CPC .... *G01N 35/00594* (2013.01); *G01N 35/00871* (2013.01); *G01N 2035/009* (2013.01); *Y10T 436/12* (2015.01); *Y10T 436/2575* (2015.01)

(58) Field of Classification Search
CPC ................... G01N 2035/009; G01N 35/00871
See application file for complete search history.

(56) References Cited

U.S. PATENT DOCUMENTS

| | | | |
|---|---|---|---|
| 4,893,515 A | 1/1990 | Uchida | |
| 5,629,207 A | 5/1997 | Seto et al. | |
| 5,762,769 A * | 6/1998 | Gotsu et al. | 204/400 |
| 5,966,676 A | 10/1999 | Fujiwara et al. | |
| 6,121,049 A * | 9/2000 | Dorenkott et al. | 436/50 |
| 6,456,944 B1 | 9/2002 | Burkhardt et al. | |
| 6,629,060 B2 | 9/2003 | Okuno et al. | |
| 2003/0154044 A1 | 8/2003 | Lundstedt et al. | |

FOREIGN PATENT DOCUMENTS

| | | |
|---|---|---|
| EP | 0726466 A1 | 8/1996 |
| EP | 1391734 A2 | 2/2004 |
| JP | 04-001570 A | 1/1992 |
| JP | 06-027120 A | 2/1994 |
| JP | 07-198726 A | 8/1995 |

(Continued)

OTHER PUBLICATIONS

European Search Report for European Application No. 05012966.7, dated Dec. 18, 2006, 4 pages.

*Primary Examiner* — P. Kathryn Wright
(74) *Attorney, Agent, or Firm* — Brinks Gilson & Lione

(57) ABSTRACT

A clinical specimen processing apparatus that includes: a preparation device that is configured to conduct operations to perform predetermined processing of clinical specimen; a controller in communication with the preparation device, wherein the controller is configured to detect an operating condition of the preparation device which performs the predetermined processing; a central processing unit that is configured to: 1) compare a detection value detected by the controller to a first threshold value and a second threshold value; and 2) determine whether or not the preparation device is in any one of three condition stages.

9 Claims, 16 Drawing Sheets

(56) References Cited

FOREIGN PATENT DOCUMENTS

| | | |
|---|---|---|
| JP | 10-215494 A | 8/1998 |
| JP | 10-229587 A | 8/1998 |
| JP | 10-308737 A | 11/1998 |
| JP | 2000-258422 A | 9/2000 |
| JP | 2001-004635 A | 1/2001 |
| JP | 2001-229291 A | 8/2001 |
| JP | 2002-335587 A | 11/2002 |
| JP | 2002-350451 A | 12/2002 |
| JP | 2003-083960 A | 3/2003 |
| JP | 2003-294763 A | 10/2003 |

* cited by examiner

| No. | ID | Date | Time | ErrorCode |
|---|---|---|---|---|
| 153 | SP-1000i^13713^11001 | 2004/2/21 | 16:15:39 | 225111 |
| 154 | SP-1000i^13713^11001 | 2004/2/21 | 16:20:12 | 225111 |
| 155 | SP-1000i^13713^11001 | 2004/2/21 | 16:35:22 | 141001 |

CLINICAL SPECIMEN PROCESSING APPARATUS AND CLINICAL SPECIMEN PROCESSING SYSTEM

RELATED APPLICATIONS

This application is a continuation application of U.S. application Ser. No. 11/155,439 filed Jun. 17, 2005, now U.S. Pat. No. 7,776,271 which claims priority under 35 U.S.C. §119 to Japanese Patent Application No. 2004-179051 filed Jun. 17, 2004, the entire content of which is hereby incorporated by reference.

BACKGROUND

1. Field of the Invention

The present invention relates to a clinical specimen processing apparatus and clinical specimen processing system, and more specifically relates to clinical specimen processing apparatus and clinical specimen processing system which can be connected to a maintenance management device over a network.

2. Description of the Related Art

Automatic analyzers are known which process measurement time-courses and measurement results, or analyzer abnormalities and measurement operation abnormalities in electronic mail, which is then transmitted to a predetermined destination (for example, refer to Japanese Laid-Open Patent Publication No. 10-308737).

Japanese Laid-Open Patent Publication No. 10-308737 discloses an automatic analyzer which normally transmits measurement time-courses and measurement results in electronic mail with a predetermined timing to a predetermined destination, such as a personal computer or the like used by the user of the analyzer, and which, when an abnormality occurs in the analyzer, rapidly transmits data representing the content of the device abnormality in an electronic mail to the predetermined destination, such as a users personal computer, without waiting for the predetermined timing. In this way the user of the automatic analyzer disclosed in Japanese Laid-Open Patent Publication No. 10-308737 is quickly made aware of the abnormality when an abnormality occurs in the automatic analyzer.

Also known are blood smear preparation apparatuses which prepare smear specimens of blood samples, and blood corpuscle analyzers (blood analyzers) which analyze blood samples for the number of blood corpuscles, hematocrit, hemoglobin or the like. In these clinical specimen processing apparatuses, adjustments are required when components gradually deteriorate with use. For example, normal operations cannot be performed when a component deteriorates, which necessitates halting the operation of the apparatus for component replacement and adjustment. In the art of the aforesaid patent publication, the user or the like is notified of the abnormal condition of the apparatus.

Since component deterioration generally progresses gradually, the operation of the apparatus may be within a tolerance range ('tolerance condition' hereafter) for some time, but the specimen processing results may be affected because the apparatus is not operating normally up until the previously mentioned abnormality occurs. When an apparatus in this tolerance condition is used continuously, the operational performance also continues inexorably until an abnormality occurs, at which point the operation of the apparatus must be stopped. If one is aware of the tolerance condition of the apparatus, it is possible to perform apparatus maintenance and parts replacement before the abnormality occurs, so as to reduce the number of times the operation of the apparatus must be stopped, although art for detecting the tolerance condition of the apparatus is not disclosed in the aforesaid patent publication.

SUMMARY OF THE INVENTION

An object of the present invention is to eliminate the previously mentioned problems by providing a clinical specimen processing apparatus and clinical specimen processing system capable of recognizing whether or not an apparatus is in an operation tolerance limit condition of the apparatus without affecting the sample processing results although the apparatus is not operating normally.

The clinical specimen processing apparatus of a first aspect of the invention provides a clinical specimen processing apparatus including an operation means for conducting operations to perform predetermined processing of clinical specimen; a detection means for detecting a operating condition of the operation means which performs the predetermined processing; comparison means for comparing a detection value detected by the detection means to a first threshold value and a second threshold value; and a determination means for determining whether or not the operation means is in any one of three condition stages.

The clinical specimen processing apparatus of a second aspect of the invention provides a clinical specimen processing apparatus including an operation means for conducting operations to perform predetermined processing of clinical specimen; a detection means for detecting a operating condition of the operation means which performs the predetermined processing; and a determination means for determining whether or not the operation means is in one among a normal condition, a first abnormal condition in which operation may be continued, and a second abnormal condition in which operation cannot be continued.

The clinical specimen processing system of a third aspect of the invention provides a clinical specimen processing system including a clinical specimen processing apparatus having a plurality of operation means for conducting operations to perform predetermined processing of clinical specimen; a detection means for detecting the operating condition of each of the operation means; a determination means capable of determining when an operation means is not in a normal condition but is in a tolerance limit condition and still capable of operation based on the detection result; and a transmission means for transmitting information representing the tolerance limit condition when the determination result for a specific operation means is a tolerance limit condition; and a management device including: a receiving means for receiving information transmitted by the transmission means; and an information analyzing means for analyzing the received information.

DETAILED DESCRIPTION OF THE PREFERRED EMBODIMENTS

The embodiments of the present invention are described hereinafter based on the drawings.

Figure 1:
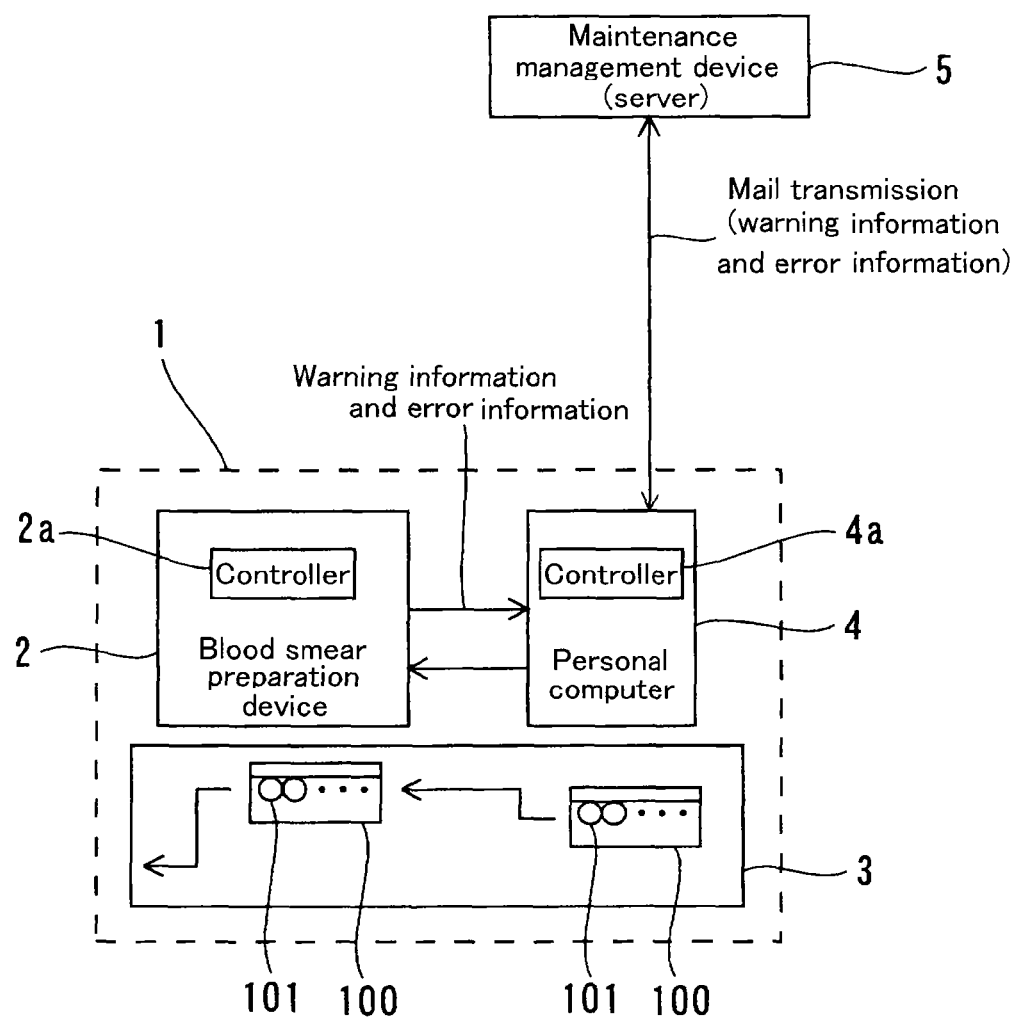
FIG. 1 is a plan view showing the general structure of a clinical specimen processing system provided with a clinical specimen processing apparatus and external maintenance management device in an embodiment of the present invention.
Figure 2:
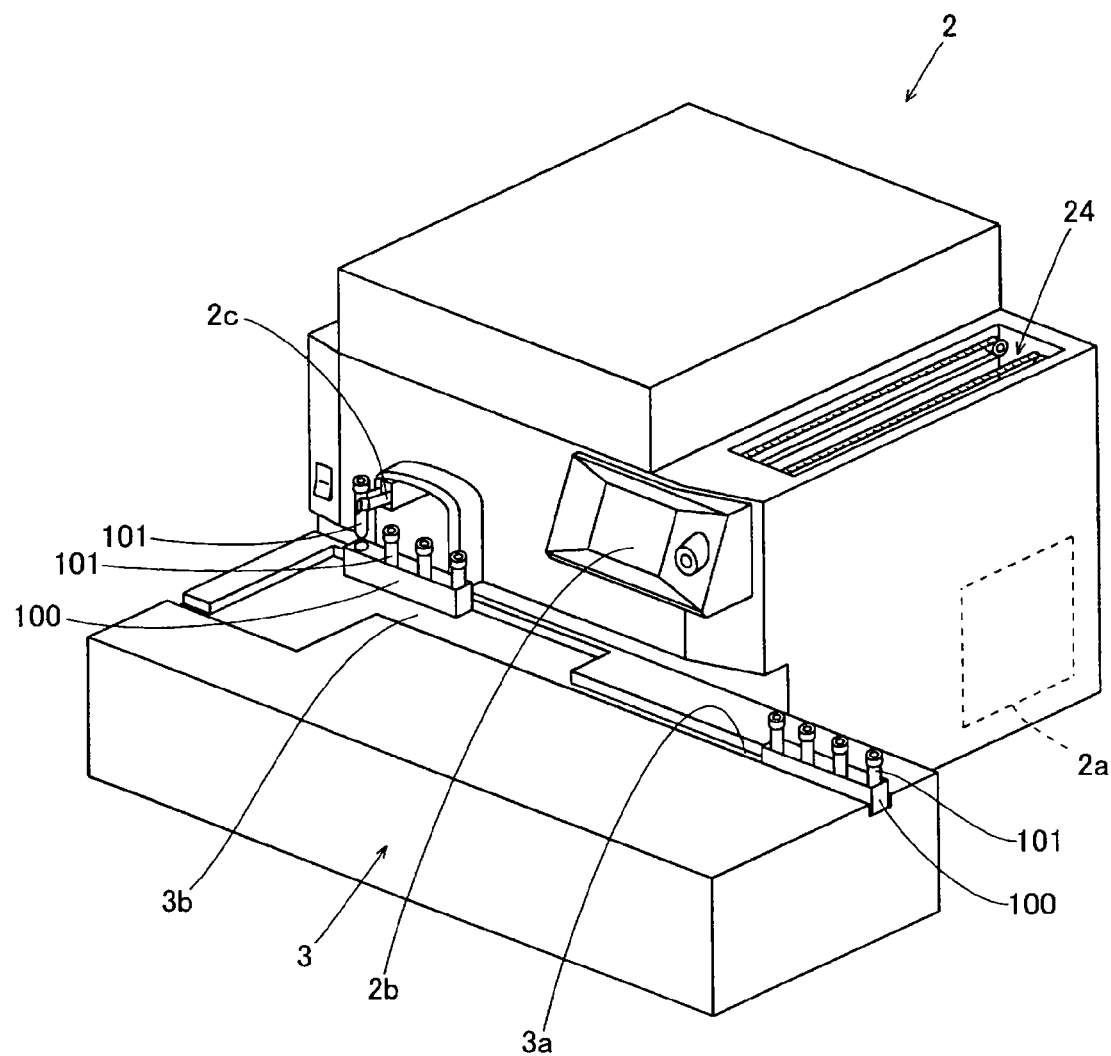
FIG. 2 is a perspective view of a blood smear preparation device and transport device in the embodiment of the present invention shown in FIG. 1.
Figure 3:
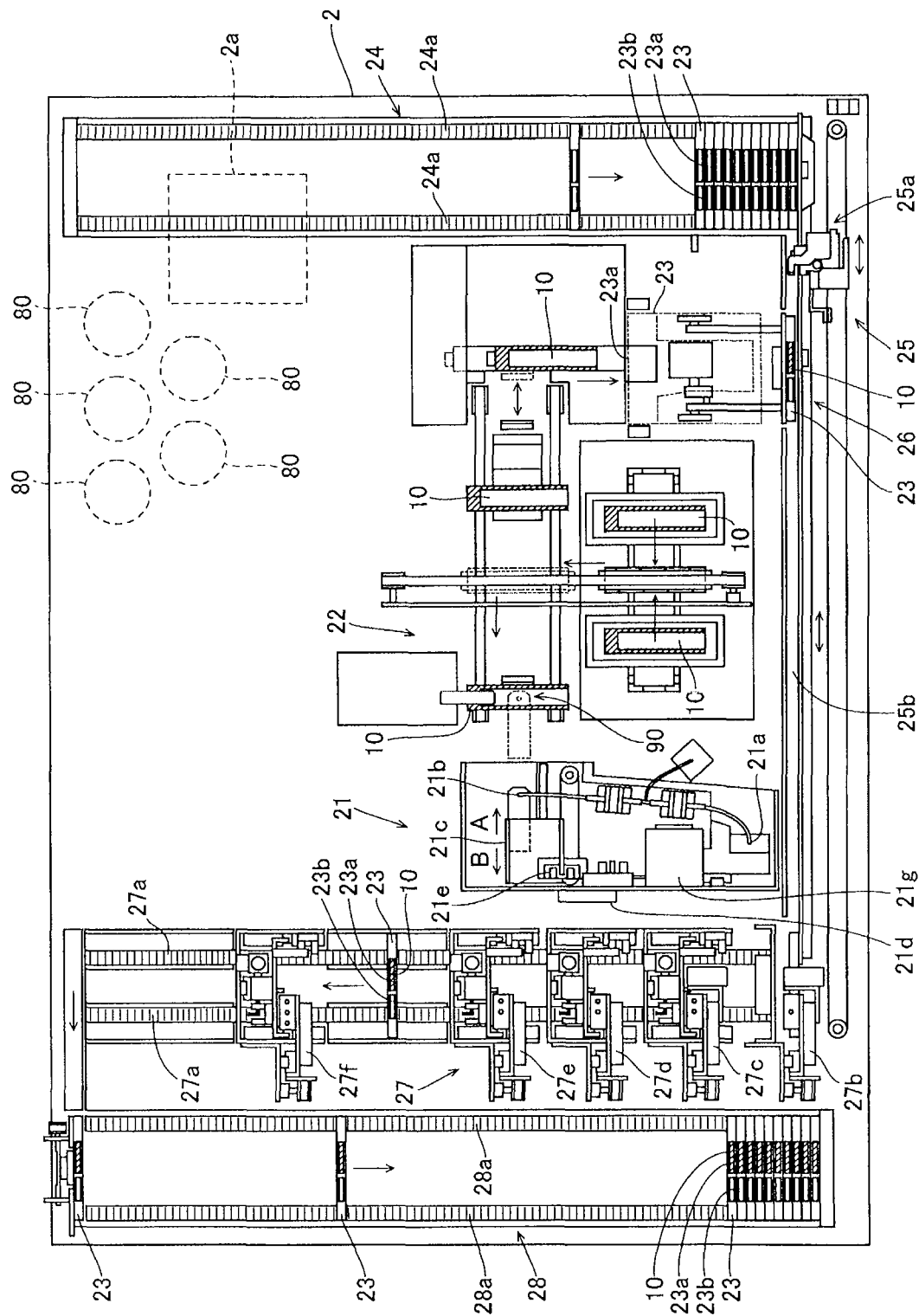
FIG. 3 is a plan view showing the internal structure of the blood smear preparation device shown in FIG. 2.
Figure 4:
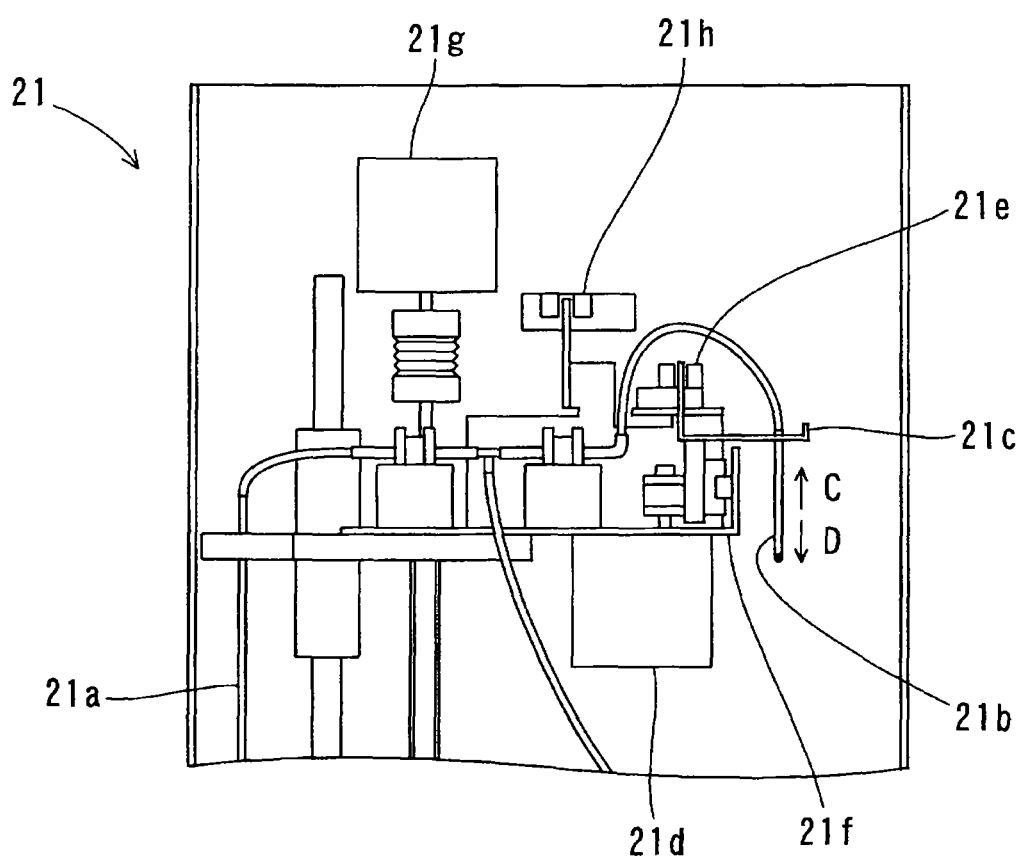
FIG. 4 is a plan view showing the suctioning/dispensing mechanism of the blood smear preparation device shown in FIG. 3.
Figure 5:
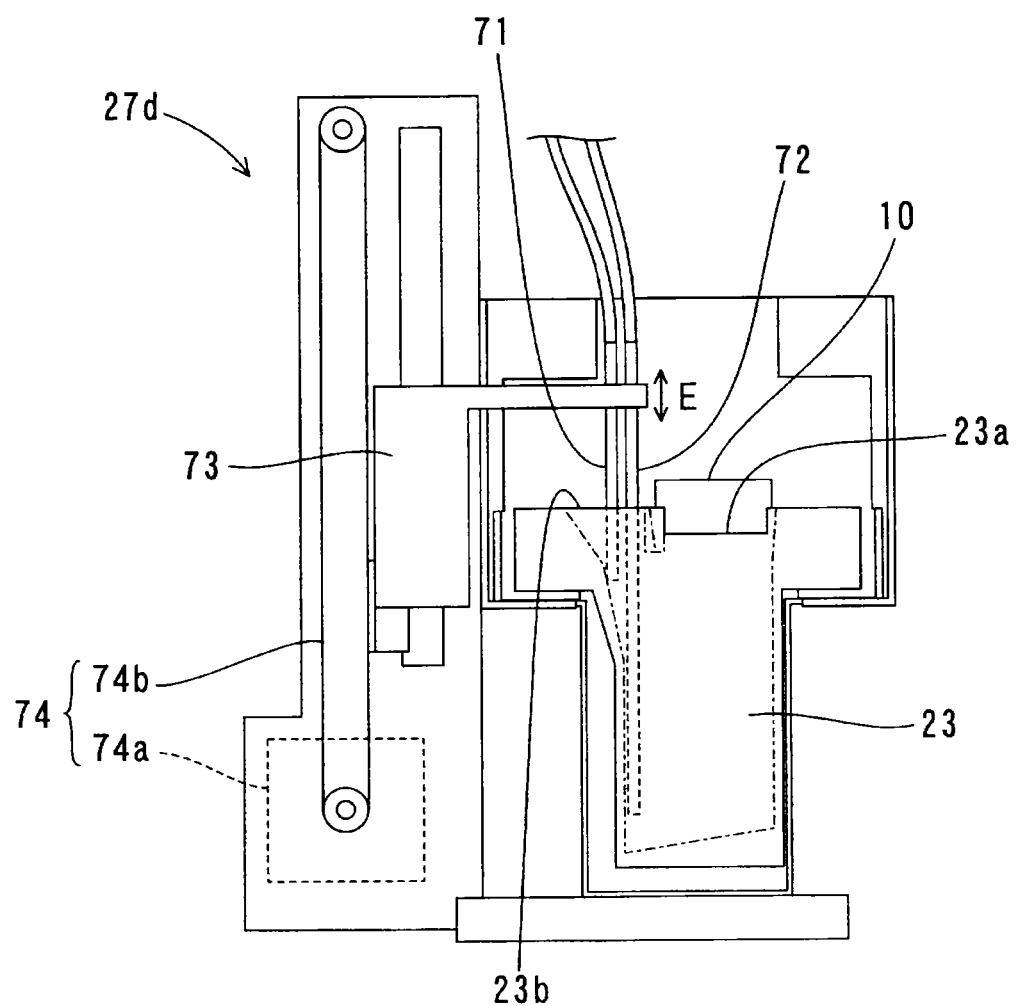
FIG. 5 is a plan view showing the third suction discharge unit of the staining section of the blood smear preparation device of FIG. 3.
Figure 6:
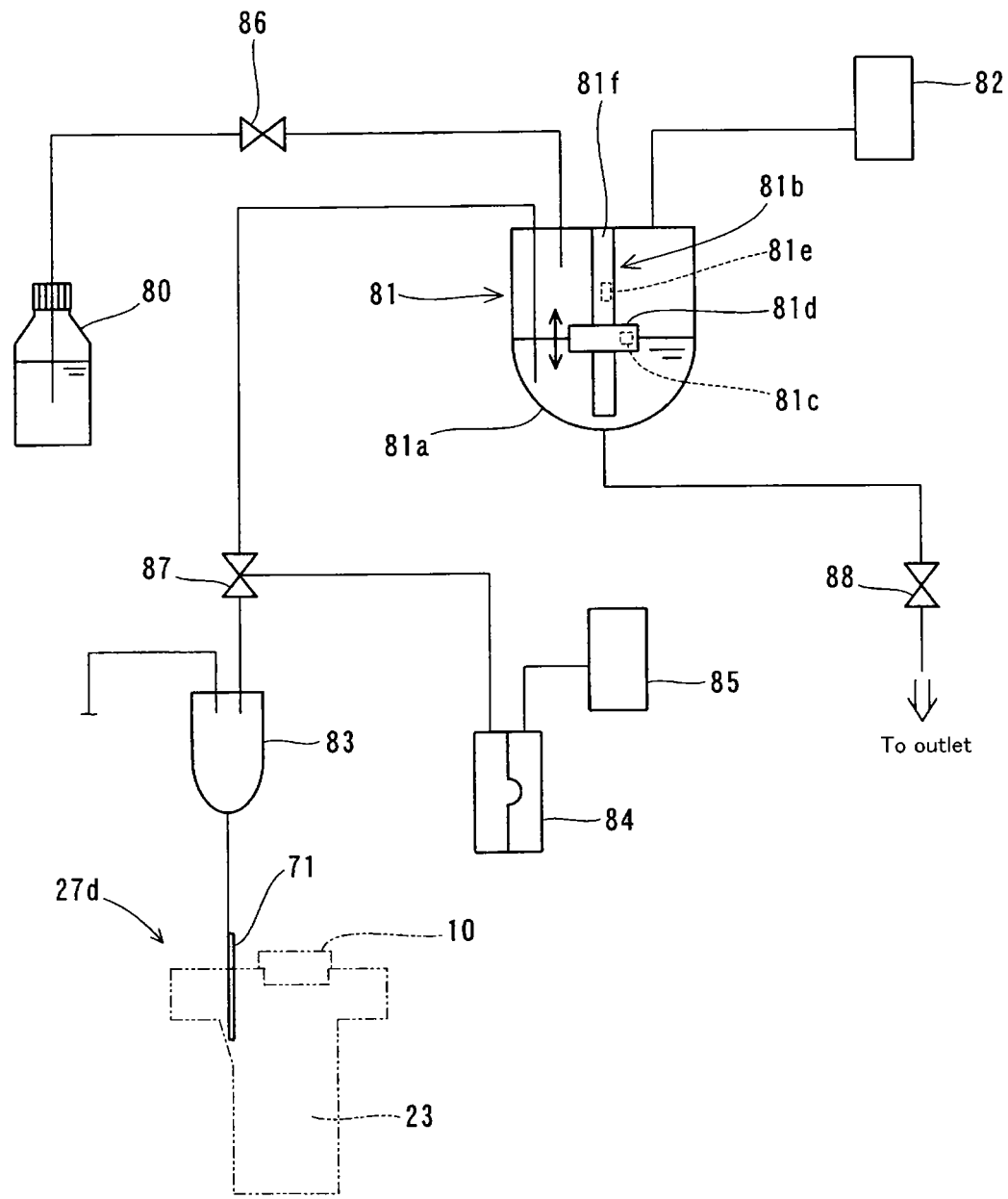
FIG. 6 is a fluid flow path diagram showing the supply path of the staining fluid supplied to the third suction discharge unit of the staining section of FIG. 5.

FIG. 1 is a plan view showing the general structure of a clinical specimen processing system provided with a clinical specimen processing apparatus and external maintenance management device in an embodiment of the present invention, and FIG. 2 is a perspective view of a blood smear preparation device and transport device. FIGS. 3 through 5 illustrate the structure of the blood smear preparation device, and FIG. 6 is a fluid flow path diagram showing the supply path of the staining fluid supplied to the third suction discharge unit of the staining section of the blood smear preparation device.

The general structure of the clinical specimen processing apparatus 1 of the present embodiment is described below with reference to FIG. 1. The clinical specimen processing apparatus 1 of this embodiment is provided with a blood smear preparation device 2, transport device 3, and personal computer 4, as shown in FIG. 1. The personal computer 4 is connected over a network to a maintenance management device (server) 5 installed off-site at a maintenance company. The clinical specimen processing system is configured by the clinical specimen processing apparatus 1, blood smear specimen preparation device 2, transport device 3, personal computer 4, and maintenance management device (server) 5. A dedicated network such as a telephone line or the like, or a network such as the internet, intranet, LAN or the like may be used as the aforesaid network.

The blood smear preparation device 2 is provided to prepare smear specimens of blood samples. The blood smear preparation device 2 includes a controller 2a, and is connected to the personal computer 4. In the present embodiment, the controller 2a of the blood smear preparation device 2 is configured as a CPU, ROM, RAM and the like. The controller 2a has a function of performing the operation control of the blood smear preparation device 2, a function of determining the occurrence of an abnormal condition in the blood smear preparation device 2, a function of determining the occurrence of a warning condition in which there is a high possibility of future impairment compared to the normal condition of the blood smear preparation device 2, and a function of transmitting information on the abnormality condition and warning condition (abnormal information and warning information) of the blood smear preparation device 2 to the personal computer 4. Furthermore, the transport device 3 is installed on the front of the blood smear preparation device 2, and has an input unit 3a and a pick-up unit 3b. The transport device 3 is provided to automatically convey a sample rack 100, which accommodates test tubes 101 containing blood, to the blood smear preparation device 2.

Figure 16:
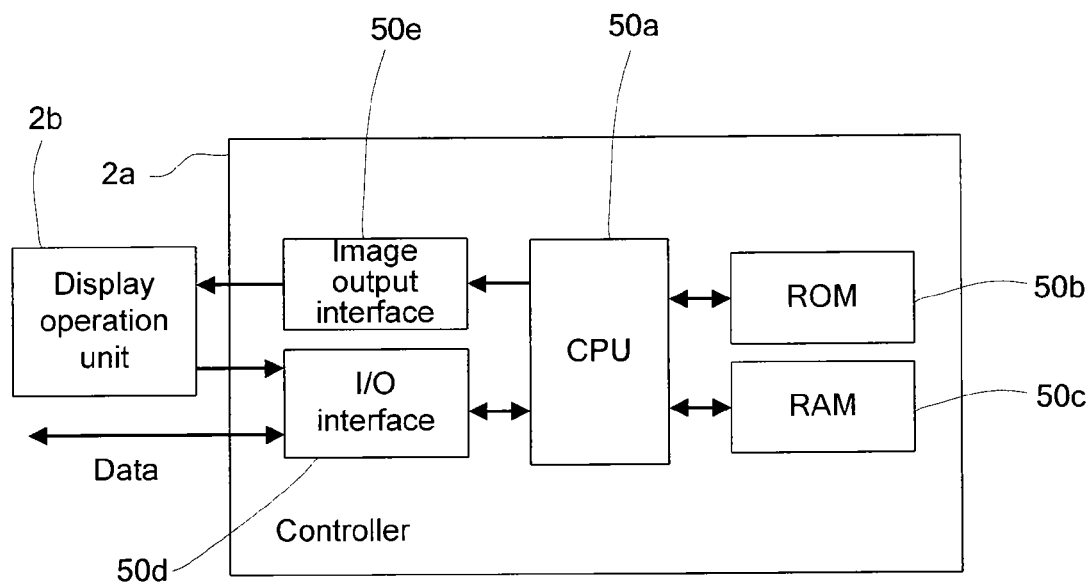
FIG. 16 is a block diagram showing the hardware structure of the controller of the blood smear preparation device of FIG. 1.

The structure of the controller 2a is described in greater detail below using FIG. 16. The controller 2a is mainly configured by a CPU 50a, ROM 50b, RAM 50c, I/O interface 50d, and image output interface 50e, which are respectively connected by a bus. The CPU 50a is capable of executing programs stored in the ROM 50b and programs loaded in the RAM 50c. The ROM 50b is a mask ROM, PROM, EPROM, EEPROM or the like, and stores programs executed by the CPU 50a, and data and the like used by the programs. The RAM 50c is an SRAM or DRAM or the like. In the present embodiment, the RAM 50c is a nonvolatile RAM. The RAM 50c is used when reading the programs stored in the ROM 50c. The RAM 50c is also used as the work area of the CPU 50a when programs are executed. The CPU 50a reads the programs stored in the ROM 50b to the RAM 50c, and displays an operation screen and setting screen on the display operation unit 2b of the blood smear preparation device 2 through the image output interface 50e. The input information, such as settings and the like, from the display operation unit 2b of the blood smear preparation device 2 is transmitted to the CPU 50a through the I/O interface 50d, and stored in the RAM 50c. The CPU 50a exchanges data with the personal computer 4 through the I/O interface 50d.

In the present embodiment, the personal computer 4 is provided with a controller 4a for transmitting the condition information (abnormality information and warning information) of the blood smear preparation device 2 to the maintenance management device (server) 5, and the controller 4a includes a memory for saving the condition information (abnormality information and warning information) of the blood smear preparation device 2. The controller 4a of the personal computer 4 includes a CPU, ROM, RAM and the like. The controller 4a of the personal computer 4 stores programs for transmitting and receiving and processing electronic mail.

Figure 17:
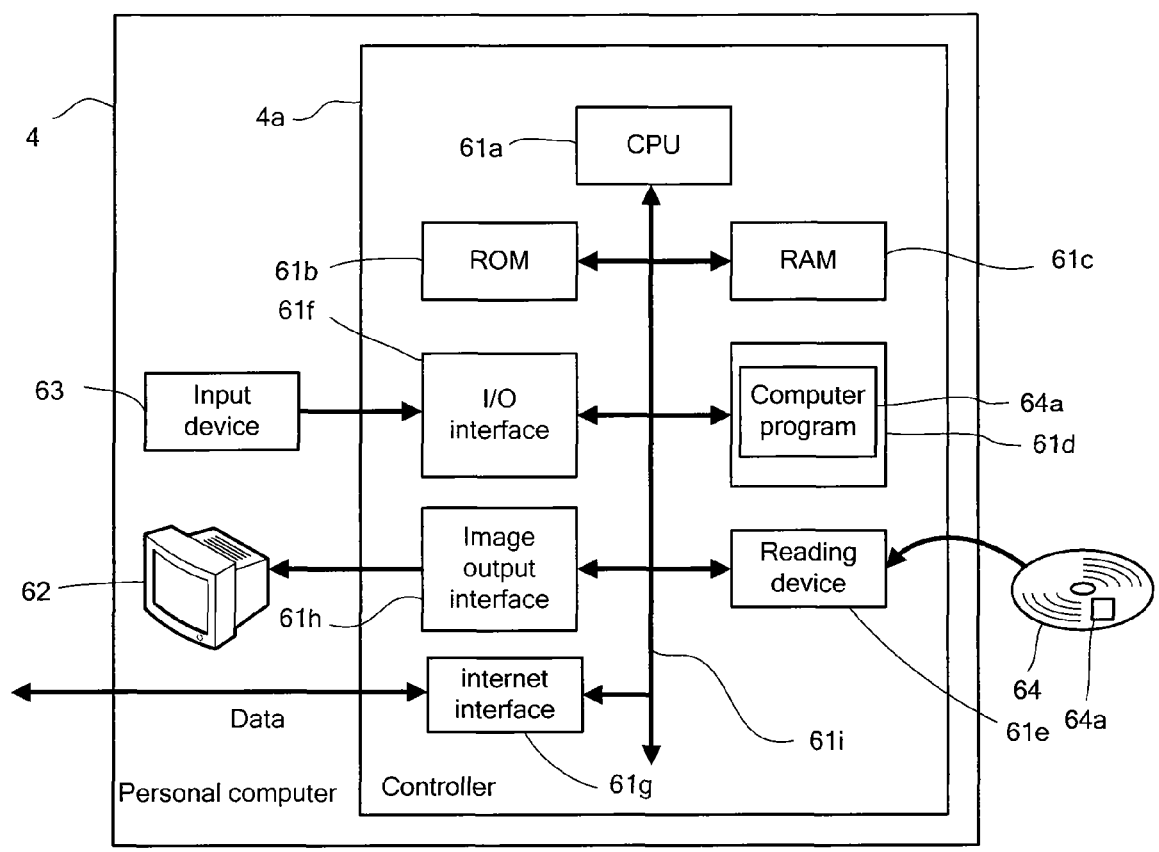
FIG. 17 is a block diagram showing the hardware structure of the personal computer of FIG. 1.

The structure of the personal computer 4 is described below in greater detail using FIG. 17. The personal computer 4 is mainly configured by a controller 4a, display 62, and input unit 63. The controller 4a is mainly configured by a CPU 61a, ROM 61b, RAM 61c, hard disk 61d, reading device 61e, I/O interface 61f, and image output interface 61h, which are connected through a bus. The CPU 61a is capable of executing computer programs stored in the ROM 61b, and computer programs loaded in the RAM 61c. The ROM 61b is a mask ROM, PROM, EPROM, EEPROM or the like, and stores programs executed by the CPU 61a, and data and the like used by the programs. The RAM 61c is an SRAM or DRAM or the like. The RAM 61c is used when reading computer programs stored in the ROM 61b and the hard disk 61d. The RAM 61c is used as the work area of the CPU 61a when the computer programs are executed. The hard disk 61d contains the installed operating system, application programs and the like, and the various computer programs and data used in the execution of the computer programs executed by the CPU 61a. The hard disk 61d also stores an electronic mail client program (MUA) for sending, receiving, and processing electronic mail. The reading device 61e is configured mainly by a floppy disk drive CD-ROM drive, or DVD-ROM drive or the like, and is capable of reading the computer program 64a or data stored on a portable storage medium 64. The CPU 61a exchanges data with the blood smear preparation device 2 through the I/O interface 61f. A communication interface 61g is, for example, and internet interface, which provides a connection which allows data communication between the personal computer 4 and the maintenance management device (server) 5 over a network. A CPU 71a exchanges data with the maintenance management device (server) 5 through a communication interface 61g.

Figure 18:
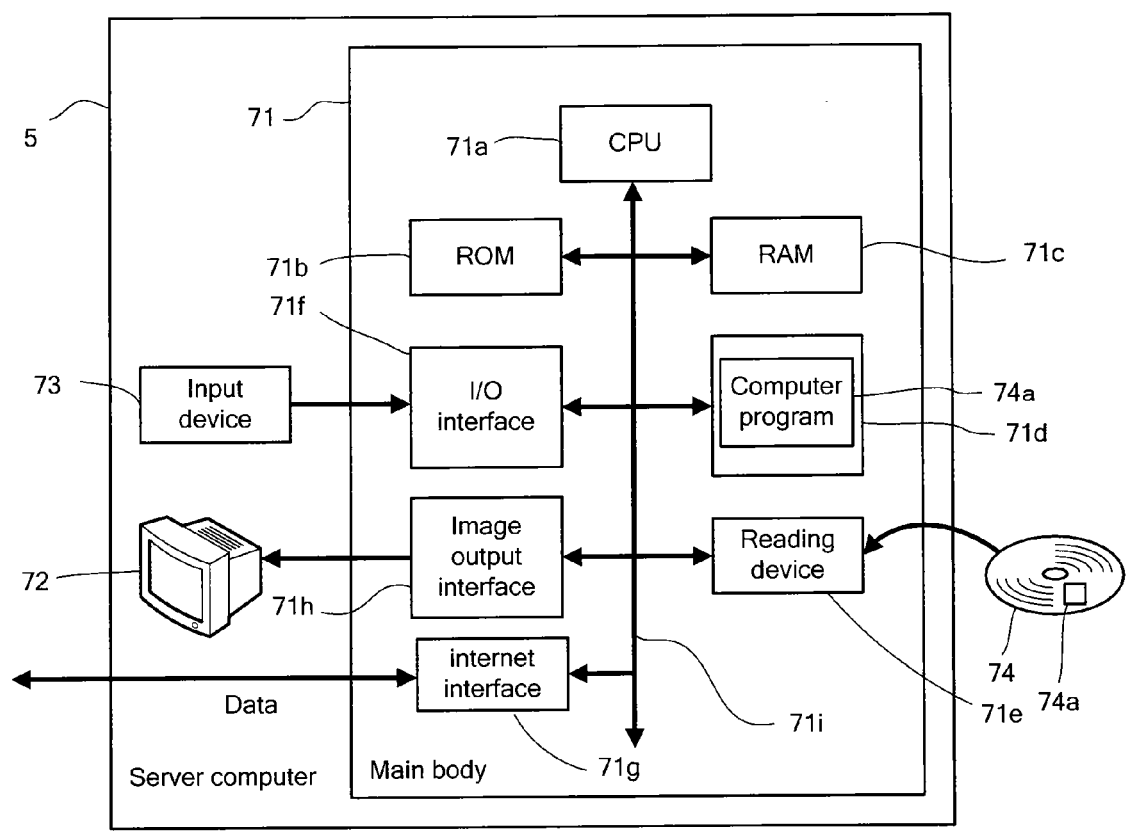
FIG. 18 is a block diagram showing the hardware structure of the maintenance management device (server) of FIG. 1.

The structure of the maintenance management device (server) 5 is described below using FIG. 18. The server 5 is configured mainly by a body 71, display 72, and input unit 73. The body 71 is mainly configured by a CPU 71a, ROM 71b, RAM 71c, hard disk 71d, reading device 71e, I/O interface 71f, image output interface 71h, and communication interface 71g, which are connected through a bus 71i. The CPU 71a is capable of executing computer programs stored in the ROM 71b, and computer programs loaded in the RAM 71c. The ROM 71b is a mask ROM, PROM, EPROM, EEPROM or the like, and stores computer programs executed by the CPU 71a, and data and the like used by the programs. The RAM 71c is an SRAM or DRAM or the like. The RAM 71c is used when reading computer programs stored in the ROM 71b and the hard disk 71d. The RAM 71c is used as the work area of the CPU 71a when the computer programs are executed. The hard disk 71d contains the installed operating system, application programs and the like, and the various computer programs and data used in the execution of the computer programs executed by the CPU 61a, The reading device 71e is configured mainly by a floppy disk drive, CD-ROM drive, or DVD-ROM drive or the like, and is capable of reading the computer program 74a or data stored on a portable storage medium 74. The communication interface 71g is, for example, an internet interface, and is connected so as to allow data communication between the maintenance management device (server) 5 and the personal computer 4 over a network. The CPU 71a exchanges data with the personal computer 4 through the communication interface 71g.

The overall structures of the blood smear preparation device 2 and transport device 3 are described below with reference to FIGS. 2 through 6. As shown in FIG. 2, the blood smear preparation device 2 is provided with, in addition to the controller 2a, a touch panel display operation unit 2b, and member 2c for conveying test tubes 101 containing blood from the transport device 3 side to the blood smear preparation device 2 side. As shown in FIG. 3, the blood smear preparation device 2 is provided with is provided with a suction/dispensing mechanism 21, smearing unit 22, resin cassette 23, cassette holder 24, cassette conveyor 25, slide glass insertion unit 26, staining unit 27, and storage unit 28. As shown in FIG. 3, below the blood smear preparation device 2 are disposed a plurality of containers 80 which contain staining solution and rinse water and the like used in the staining unit 27.

The suction/dispensing mechanism 21 has the functions of suctioning blood from the test tube 101 conveyed to blood smear preparation device 2 side by the hand member 2c (refer to FIG. 2), and dispensing the suctioned blood to the slide glass 10. As shown in FIG. 4, the suction/dispensing mechanism 21 includes a piasa (aspiration needle) 21a for suctioning blood from the test tube 101 (refer to FIG. 2), dispensing pipette 21b for dispensing the suctioned blood to the slide glass 10, support member 21c for supporting the dispensing pipette 21b, front-back drive motor 21d for moving the support member 21c forward (arrow A direction in FIG. 3) and backward (arrow B direction in FIG. 3), sensor 21e for detecting the home position of the dispensing pipette 21c in the horizontal position by detecting a specific part of the support member 21c, support member 21f for supporting the support member 21c and the front-back drive motor 21d, raise-lower drive motor 21g for moving the support member 21f upward (arrow C direction in FIG. 3) and downward (arrow D direction in FIG. 3), and sensor 21h for detecting the home position of the dispensing pipette 21c in the vertical position by detecting a specific part of the support member 21f.

As shown in FIG. 3, the smearing unit 22 is provided to supply a slide glass 10 to the dispensing/smearing position 90, smear and dry the blood dispensed on the slide glass 10, and label the slide glass 10. The resin cassette 23 is constructed to be capable of accommodating the smeared slide glass 10 and the fluid (staining solution) used in the staining process. The cassette 23 includes a slide glass hole 23a, and staining solution dispensing hole 23b, as shown in FIG. 5. The slide glass hole 23a and the staining solution dispensing hole 23b are internal.

As shown in FIG. 3, the cassette holder 24 is provided to accept a cassette 23 in the cassette carrier 25, and includes a conveyor belt 24a. Furthermore, the cassette carrier 25 is provided to convey a cassette 23 loaded in the cassette holder 24 to the slide glass insert unit 26 and the staining unit 27. The cassette carrier 25 includes a cassette transport member 25a which is movable in a horizontal direction, and a transport path 25b to transport a cassette 23 supplied from the cassette holder 24, as shown in FIG. 3. Furthermore, the slide glass insert unit 26 shown in FIG. 3 is provided to accommodate a slide glass 10, which has been smeared and labeled, in a slide glass hole 23a.

The staining unit 27 shown in FIG. 3 is provided to stain a smeared slide glass 10 by supplying a staining solution to a staining solution suction/dispensing hole 23b of the cassette 23 transported by the cassette transport member 25a. The staining unit 27 includes a conveyor belt 27a for transporting the cassette 23, and first through fifth suction and discharge units 27a to 27f for supplying and discharging staining solution to and from the cassette 23.

Using the third suction and discharge unit 27d as an example selected from among the first through fifth suction and discharge units 27b to 27f, the structure of the third suction and discharge unit 27d and the staining solution flow path used by the third suction and discharge unit 27d are described below with reference to FIGS. 5 and 6. As shown in FIG. 5, the third suction and discharge unit 27d includes a supply pipette 71 and discharge pipette 72 for supplying and discharging staining solution to the cassette 23, pipette support member 73 for supporting the supply pipette 71 and discharge pipette 72, and a drive mechanism 74 provided with a motor 74a and drive belt 74b for moving the cassette support member 73 in vertical directions (arrow E direction in FIG. 5). The third suction and discharge unit 27d is constructed so as to supply and discharge staining solution to the cassette 23 by moving the supply pipette 71 and discharge pipette 72 in vertical directions using the drive mechanism 74.

Next, the flow path for supplying staining solution from the supply pipette 71 of the third suction and discharge unit 27d includes, as shown in FIG. 6, a chamber 81 for temporarily storing the staining solution, pressure regulator 82 for increasing and decreasing the pressure in the chamber 81, mixing chamber 83 for mixing the staining solution with a diluent for diluting the staining solution, diaphragm pump 84 for moving the staining solution between the chamber 81 and the mixing chamber 83, and pressure regulator 85 for increasing and decreasing the pressure in the diaphragm pump 84. The chamber 81 is connected to the container 80, pressure regulator 82, mixing chamber 83, and outlet by means of pipes. The mixing chamber 83 is connected to the supply pipette 71 of the third suction and discharge unit 27d of the staining unit 27 by means of pipes. Furthermore, pipes 86, 87, and 88 are respectively provided between the container 80 and chamber 81, the chamber 81 and mixing chamber 83, and the chamber 81 and the outlet. The diaphragm pump 84 is connected to a valve 87 by means of a pipe. The mixing chamber 83 is connected to a pipe which supplies diluent for diluting the staining solution.

The chamber 81 has storage unit 81a which contains staining solution, and a float switch 81b provided within the storage unit 81a, as shown in FIG. 6. The float switch 81b is formed of a material capable of floating on the staining solution, and is configured by a float member 81d within which is embedded a magnet 81c, and a support rod 81f which has an internal reed switch 81e of the magnetic contact type to support the float member 81d so as to be movable in vertical directions. Furthermore, the reed switch 81e is embedded at a predetermined position in the support rod 81f and is capable of detecting thee magnetic force of the magnet 81c of the float member 81d when the staining solution reaches a stipulated amount within the storage unit 81a. The float switch 81b is constructed so as to be turned ON when the magnetic force of the magnet 81c within the float member 81d is detected by the reed switch 81e of the support rod 81f when the float member 81d is near a predetermined position, and be turned OFF when the magnetic force of the magnet 81c within the float member 81d is not detected by the reed switch 81e of the support rod 81f when the float member 81d is removed from the predetermined position.

The storage unit 28 shown in FIG. 3 is provided to store the cassette 23 which contain slide glasses 10 stained by the staining unit 27. The storage unit 28 is provided with a conveyor belt 28a for transporting the cassette 23.

The operation of the clinical specimen processing apparatus 1 of the present embodiment is described below with reference to FIGS. 1 to 4 and FIGS. 6 to 10. First, the clinical chart information of the person (patient) who supplied the specimen is input to a host computer not shown in the drawing. Then, the blood smear preparation device 2 shown in FIGS. 1 and 2 collects a blood specimen from a test tube 101 held in the sample rack 100 transported by the transport device 3, and prepares a blood smear specimen in accordance with the information from the host computer.

When a blood smear specimen is prepared by the blood smear preparation device 2, in an initial suction and dispensing operation, the sample rack 100, which holds test tubes 101 containing blood samples, is placed in the input unit 3a of the transport device 3, as shown in FIG. 2. Then, an automatic suction start switch displayed on the display operation unit 2b is pressed. In this way the sample rack 100 is transported to the pick-up unit 3b of the transport device 3. Then, after the hand member 2c of the blood smear preparation device 2 lifts and agitates the test tube 101 of the sample rack 100, the test tube 101 is disposed in the suction/dispensing mechanism 21 as shown in FIG. 3. Next, the blood within the test tube 101 is suctioned by the piasa 21a. Thereafter, the dispensing pipette 21b is moved forward (arrow A direction in FIG. 3) and downward (arrow D direction in FIG. 4) to the dispensing/smearing position 90 shown in FIG. 3, and subsequently blood is titrated (dispensed) from the dispensing pipette 21b to the slide glass 10. After the dispensing operation, the dispensing pipette 21b moved upward (arrow C direction in FIG. 4) and backward (arrow B direction in FIG. 3) to return to the home position. When the dispensing pipette 21b is raised after the dispensing operation, the raise-lower drive motor 21g is driven with the dispensing pipette 21b disposed at a bottom edge position. In this way the support member 21f which supports the dispensing pipette 21b is moved in the arrow C direction in FIG. 4. Then, the drive of the raise-lower drive motor 21g is stopped when the support member 21f is detected by the sensor 21h. The operation of raising the dispensing pipette 21b is controlled by the controller 2a of the blood smear preparation device 2.

Figure 7:
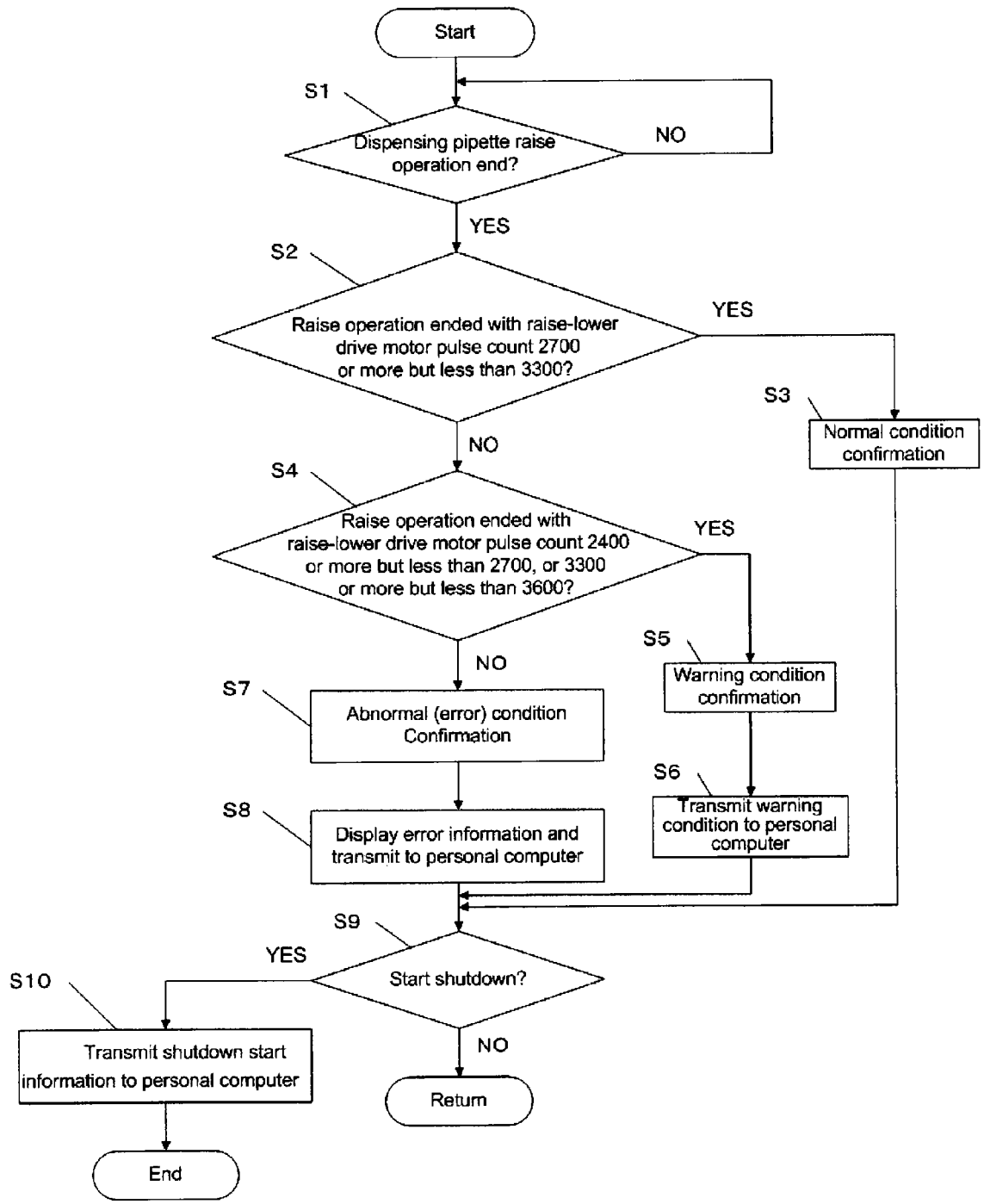
FIG. 7 is a flow chart illustrating condition verification performed by the controller of the blood smear preparation device in the operation to raise the dispensing pipette of the suction/dispensing mechanism shown in FIG. 3.

The condition verification flow by the controller 2a of the blood smear preparation device 2 in the raising operation of the dispensing pipette 21b of the present embodiment is described below with reference to FIG. 7. First, in step S1, the CPU 50a of the blood smear preparation device 2 determines whether or not the operation of raising the dispensing pipette 21b performed by the raise-lower drive motor 21g has ended; when it has been determined that the dispensing pipette 21b raising operation has ended, the routine advances to step S2. Thereafter, in step S2, the CPU 50a counts the number of pulses of the raise-lower drive motor 21g when the dispensing pipette 21b is raised (arrow C direction in FIG. 4) by the raise-lower drive motor 21g, and determines whether or not the number of pulses of the raise-lower drive motor 21g required from the start to the end of the dispensing pipette 21b raising operation is within a range of 2700 or more but less than 3300. Then, when the CPU 50a determines in step S2 that the number of pulses of the raise-lower drive motor 21g required from the start to the end of the dispensing pipette 21b raising operation is within a range of 2700 or more but less than 3300, then the CPU 50a determines that the dispensing pipette 21b raising operation is a normal condition, and the routine advances to step S9. Then, when the CPU 50a determines in step S2 that the number of pulses of the raise-lower drive motor 21g required from the start to the end of the dispensing pipette 21b raising operation is not within a range of 2700 or more but less than 3300, then the CPU 50a determines in step S4 whether the number of pulses of the raise-lower drive motor 21g required from the start to the end of the dispensing pipette 21b raising operation is within a range of more than 2400 but less than 2700, or more than 3300 but less than 3600. Then, when the CPU 50a has determined in step S4 that the number of pulses of the raise-lower drive motor 21g required from the start to the end of the dispensing pipette 21b raising operation is within a range of 2400 or more but less than 2700, or 3300 or more but less than 3600, then in step S5 a warning condition of the dispensing pipette 21b raising operation is confirmed, and error code is called from the error code table, and saved as an error log in the RAM 50c (refer to FIG. 16) of the blood smear preparation device 2. Thereafter, the routine advances to step S9. The error code table allocates error codes to various warning conditions and is prepared beforehand, and is saved in the ROM 50b of the blood smear preparation device 2.

Next, in step S6, the CPU 50a transmits warning information from the blood smear preparation device 2 to the personal computer 4. Then, when the CPU 50a has determined in step S4 that the number of pulses of the raise-lower drive motor 21g required from the start to the end of the dispensing pipette 21b raising operation is not within a range of 2400 or more but less than 2700, or 3300 or more but less than 3600, then in step S7 an abnormal (error) condition of the dispensing pipette 21b raising operation is confirmed, and error code is called from the error code table, and saved as an error log in the RAM 50c (refer to FIG. 16) of the blood smear preparation device 2. The error code table allocates error codes to various abnormal conditions and is prepared beforehand, and is saved in the ROM 50b of the blood smear preparation device 2. Then, in step S8, the CPU 50a displays an error display on the display operation unit 2b of the blood smear preparation device 2, and transmits error information to the personal computer 4, whereupon the routine advances to step S9. In step S9, the CPU 50a determines whether or not to begin shutdown. When the CPU 50a determines in step S9 to not begin shutdown, the routine returns to step S1. When the CPU 50a determines in step S9 to begin shutdown, shutdown start information is transmitted to the personal computer 4, and the blood smear preparation device 2 is shutdown and the process ends in step S10. In this way the controller 2a of the blood smear preparation device 2 can confirm the existing condition in the dispensing pipette 21b raising operation.

When the dispensing pipette 21b is moved backward after being raised, the forward-back drive motor 21d is driven with the dispensing pipette 21b set at the front end position after the raising operation by the forward-back drive motor 21d. In this way the support member 21c which supports the dispensing pipette 21b is moved in the arrow B direction in FIG. 3. Then, the drive of the forward-back drive motor 21d is stopped when the support member 21c is detected by the sensor 21e. The operation of retracting the dispensing pipette 21b is controlled by the controller 2a of the blood smear preparation device 2.

Figure 8:
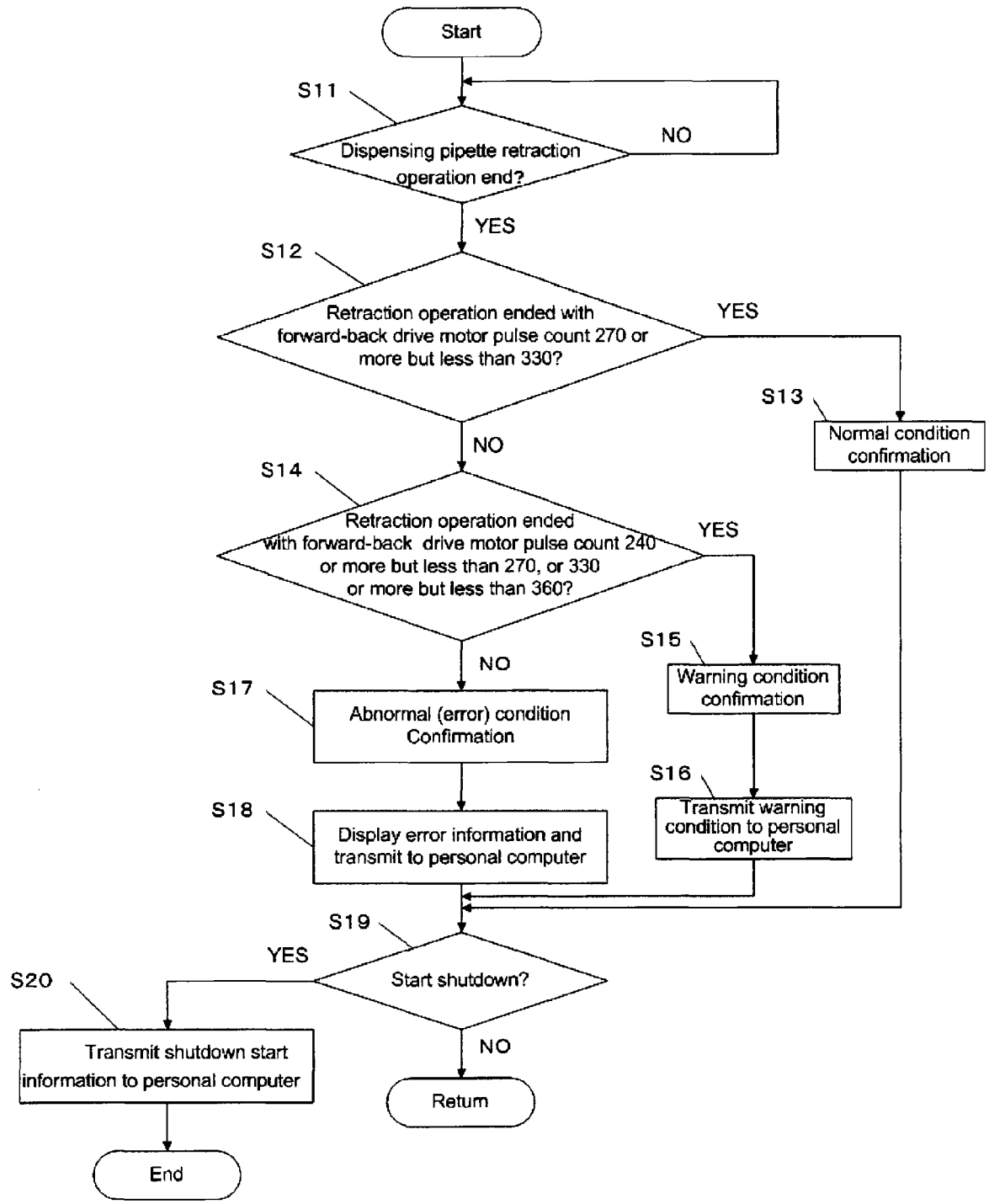
FIG. 8 is a flow chart illustrating condition verification performed by the controller of the blood smear preparation device in the operation to retract the dispensing pipette of the suction/dispensing mechanism shown in FIG. 3.

The condition verification flow by the controller 2a of the blood smear preparation device 2 in the retracting operation of the dispensing pipette 21b of the present embodiment is described below with reference to FIG. 8. First, in step S11, the CPU 50a of the blood smear preparation device 2 determines whether or not the operation of retracting the dispensing pipette 21b performed by the forward-back drive motor 21d has ended; when it has been determined that the dispensing pipette 21b retracting operation has ended, the routine advances to step S12. Thereafter, in step S22, the CPU 50a counts the number of pulses of the forward-back drive motor 21d when the dispensing pipette 21b is moved backward (arrow B direction in FIG. 3) by the forward-back drive motor 21d, and determines whether or not the number of pulses of the forward-back drive motor 21d required from the start to the end of the dispensing pipette 21b retracting operation is within a range of 270 or more but less than 330. Then, when the CPU 50a determines in step S2 that the number of pulses of the forward-back drive motor 21d required from the start to the end of the dispensing pipette 21b retracting operation is within a range of 270 or more but less than 330, then the CPU 50a determines that the dispensing pipette 21b retracting operation is a normal condition, and the routine advances to step S19. When the CPU 50a determines in step S12 that the number of pulses of the forward-back drive motor 21d required from the start to the end of the dispensing pipette 21b retracting operation is not within a range of 270 or more but less than 330, then the CPU 50a determines in step S14 whether or not the number of pulses of the forward-back drive motor 21d is 240 or more but less than 270, or 330 or more but less than 360. Then, when the CPU 50a determines in step S14 that the number of pulses of the forward-back drive motor 21d required from the start to the end of the dispensing pipette 21b retracting operation is within a range of 240 or more but less than 270, or 330 or more but less than 360, then a warning condition is confirmed for the dispensing pipette 21b retracting operation, an error code is called from the error code table and saved as an error log in the RAM 50c (refer to FIG. 16) of the blood smear preparation device 2. Thereafter, the routine advances to step S19. The error code table allocates error codes to various warning conditions and is prepared beforehand, and is saved in the ROM 50b of the blood smear preparation device 2.

Next, in step S16, the CPU 50a transmits warning information from the blood smear preparation device 2 to the personal computer 4. When the CPU 50a determines in step S14 that the number of pulses of the forward-back drive motor 21d required from the start to the end of the dispensing pipette 21b retracting operation is not within a range of 240 or more but less than 270, or 330 or more but less than 360, then an abnormal (error) condition is confirmed for the dispensing pipette 21b retracting operation, an error code is called from the error code table and saved as an error log in the RAM 50c (refer to FIG. 16) of the blood smear preparation device 2. The error code table allocates error codes to various abnormal conditions and is prepared beforehand, and is saved in the ROM 50b of the blood smear preparation device 2. Then, in step S18, the CPU 50a displays an error display on the display operation unit 2b of the blood smear preparation device 2, and transmits error information to the personal computer 4, whereupon the routine advances to step S19. In step S19, the CPU 50a determines whether or not to begin shutdown. When the CPU 50a determines in step S19 to not begin shutdown, the routine returns to step S11. When the CPU 50a determines in step S19 to begin shutdown, shutdown start information is transmitted to the personal computer 4, and the blood smear preparation device 2 is shutdown and the process ends in step S20. In this way the controller 2a of the blood smear preparation device 2 can confirm the existing condition in the dispensing pipette 21b retracting operation.

The smear operation is performed by the smearing unit 22 in parallel with the previously described suction and dispensing operation or after the suction and dispensing operation by the suction and dispensing mechanism 21. In the smearing unit 22, a slide glass 10 is supplied to the dispensing/smearing position 90 (refer to FIG. 3), and blood is titrated onto the slide glass 10, smeared and dried. After the blood sample information has been printed on the slide glass 10, the labeled slide glass 10 is moved to the slide glass insert unit 26. Next, the cassette 23 placed in the cassette holder 24 shown in FIG. 3 is conveyed to the transport path 25b of the cassette transport unit 25 by a feed belt 24a. Then, the cassette 23 is delivered to the slide glass insert unit 26 by the cassette transport member 25a of the cassette carrier 25.

In the slide glass insert unit 26 shown in FIG. 3, first a determination is made as to whether or not a slide glass 10 is set in the slide glass hole 23a of the cassette 23. When it is determined that a slide glass 10 is set in the slide glass hole 23a, the cassette is moved directly along the transport path to the staining unit 27 by the cassette transport member 25a. In this case, the cassette 23 is moved to the storage unit 28 without undergoing the staining process by the staining unit 27. Furthermore, in the slide glass insert unit 26, when is has been determined that a slide glass 10 is not set in the slide glass hole 23*a* of the cassette 23, a slide glass 10 insertion operation is performed to insert a slide glass 10 in the cassette 23 by the slide glass insert unit 26, and thereafter the cassette 23 containing the smeared slide glass 10 is transported to the staining unit 27 by the cassette transport member 25*a*.

In the staining unit 27 of the present embodiment, the cassette 23 is transported by the conveyor belt 27*a*, and in the first suction and discharge unit 27*b* through fifth suction and discharge unit 27*f*, the smeared slide glass 10 in the cassette 23 are subjected to the staining process by sequentially dispensing and suctioning rinse water and staining solution through the staining solution suction and dispensing hole 23*b* of the cassette 23. Furthermore, the fluids, such as staining solution, used in the staining process of the slide glass 10 are temporarily stored in the chamber 81, and thereafter dispensed into the cassette 23 from the supply pipette 71, as shown in FIG. 6.

Using the third suction and discharge unit 27*d* as an example selected from among the first through fifth suction and discharge units 27*b* to 27*f*, the suction operation and the discharge operation are described below for the chamber 81 which temporarily stores the staining fluid dispensed into the cassette 23 with reference to FIG. 6.

First, when the chamber 81 suction operation is performed, the valve 86 shown in FIG. 6 is opened and the valve 88 is closed, and in valve 87 the flow path is closed between the chamber 81 and the mixing chamber 83. Then, the pressure is reduced within the chamber 81 by the pressure regulator 82. In this way staining solution in the container 80 moves into the chamber 81. The float member 81*d* of the float switch 81*b* installed within the chamber 81 moves upward in conjunction with the inflowing staining solution. Then, the vacuum is released by the pressure regulator 82 when the float switch 81*b* is turned ON, and the staining solution suctioning operation by the chamber 81 ends.

When the staining solution within the chamber 81 is moved to the mixing chamber 83, the valves 86 and 88 are closed, and in the valve 87, the flow path is opened between the chamber 81 and the diaphragm pump 84. Then, the pressure is reduced within the diaphragm pump 84 by the pressure regulator 85. In this way the staining solution within the chamber 81 is suctioned at a constant rate into the diaphragm pump 84. Thereafter, in the valve 87, the flow path is opened between the diaphragm pump 84 and the mixing chamber 83. Then, the pressure is reduced within the diaphragm pump 84 by the pressure regulator 85. In this way the staining solution within the diaphragm pump 84 is moved at a constant rate to the mixing chamber 83. Then, after the staining solution is diluted in the mixing chamber 83, the staining solution is supplied from the supply pipette 71 of the third suction and discharging unit 27*d* into the cassette 23.

Furthermore, when the chamber 81 discharge operation is performed, the valve 86 is closed and the valve 88 is opened, and in the valve 87, the flow path is closed between the chamber 81 and the mixing chamber 83. Then, the pressure is increased within the chamber 81 by the pressure regulator 82. In this way the staining solution within the chamber 81 is discharged from the device through the outlet. The float member 81*d* of the float switch 81*b* installed within the chamber 81 moves downward in conjunction with the outflow of the staining solution. Then, the pressure is released by the pressure regulator 82 when the float switch 81*b* id turned OFF, and the staining solution discharge operation from the chamber 81 ends.

Figure 9:
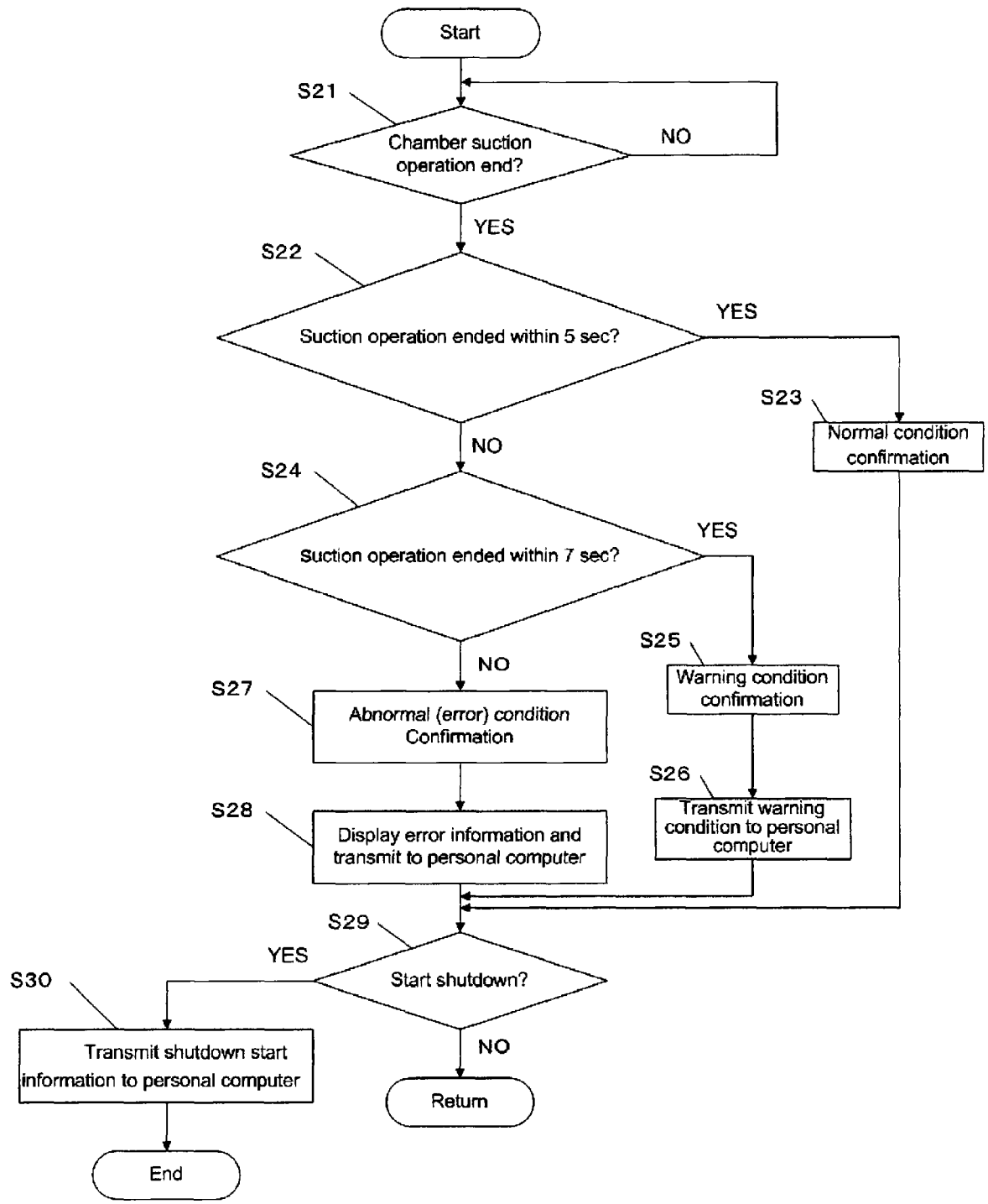
FIG. 9 is a flow chart illustrating condition verification performed by the controller of the blood smear preparation device in the chamber suctioning operation shown in FIG. 6.

The condition confirmation flow by the controller 2*a* of the blood smear preparation device 2 in the chamber 81 suction operation in the present embodiment is described below with reference to FIG. 9. First, in step S21, the CPU 50*a* of the blood smear preparation device 2 determines whether or not the chamber 81 staining solution suction operation has ended; and when it has been determined that the chamber 81 staining solution suction operation has ended, the routine advances to step S22. Thereafter, in step S22, the CPU 50*a* measures the time required from the start of the chamber 81 staining solution suction operation until the suction operation ends when the float switch 81*b* is turned ON, and determines whether or not the chamber 81 suction operation has ended by whether the float switch 81*b* has been turned On within 5 seconds. When the CPU 50*a* has determined that the chamber 81 suction operation has ended when the float switch 81*b* is turned ON within 5 seconds in step S22, then in step S23, the CPU 50*a* determines that the chamber 81 suction operation is a normal condition, and the routine advances to step S29. When the CPU 50*a* has determined that the chamber 81 suction operation has not ended and the float switch 81*b* has not been turned ON within 5 seconds in step S22, then in step S24, the CPU 50*a* determines whether or not the chamber 81 suction operation has ended when the float switch 81*b* has been turned ON within 7 seconds. When the CPU 50*a* has determined that the chamber 81 suction operation has ended when the float switch 81*b* is turned ON within 7 seconds in step S24, then in step S25, the CPU 50*a* determines that the chamber 81 suction operation is a warning condition, and an error code is called from the error code table and saved as an error log in the RAM 50*c* (refer to FIG. 16) of the blood smear preparation device 2. Thereafter, the routine advances to step S29. The error code table allocates error codes to various warning conditions and is prepared beforehand, and is saved in the ROM 50*b* of the blood smear preparation device 2.

In step S26, the CPU 50*a* of the blood smear preparation device 2 transmits the warning information from the blood smear preparation device 2 to the personal computer 4. When the CPU 50*a* has determined that the chamber 81 suction operation has not ended and the float switch 81*b* has not turned ON within 7 seconds in step S24, then in step S27, the CPU 50*a* determines that the chamber 81 suction operation is abnormal (error) condition, and an error code is called from the error code table and saved as an error log in the RAM 50*c* (refer to FIG. 16) of the blood smear preparation device 2. The error code table allocates error codes to various abnormal conditions and is prepared beforehand, and saved in the ROM 50*c* of the blood smear preparation device 2. Then, in step S28, the CPU 50*a* displays an error display on the display operation unit 2*b* of the blood smear preparation device 2, transmits the error information to the personal computer 4, and the routine advances to step S29. In step S29, the CPU 50*a* determines whether or not to begin shutdown. When the CPU 50*a* determines not to begin shutdown in step S29, the routine returns to step S21. When the CPU 50*a* determines to start shutdown in step S29, then in step S30 shutdown start information is transmitted to the personal computer 4, the blood smear preparation device 2 shuts down and the process ends. In this way the controller 2*a* of the blood smear preparation device 2 is able to confirm the condition in the chamber 81 suction operation.

Figure 10:
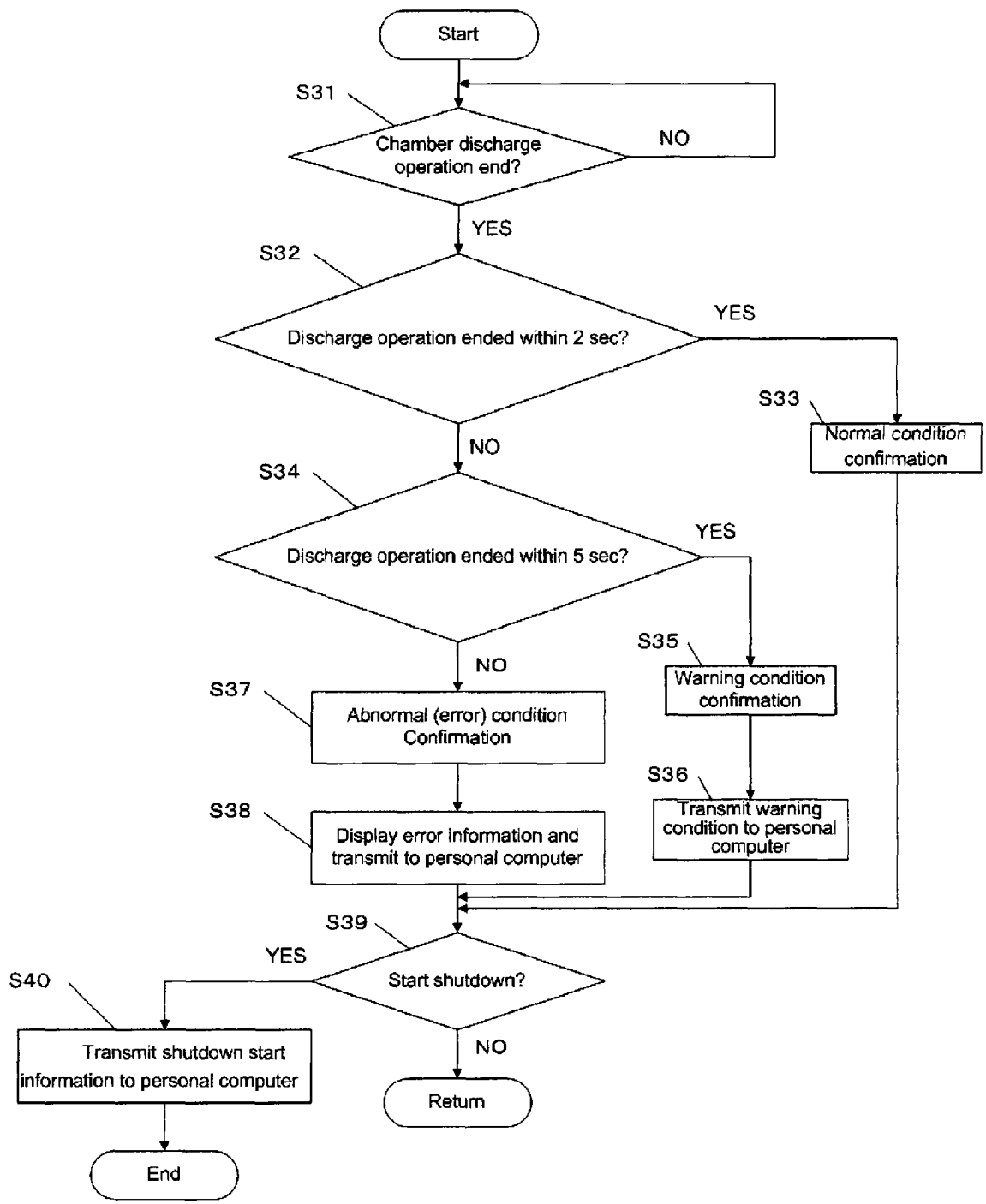
FIG. 10 is a flow chart illustrating condition verification performed by the controller of the blood smear preparation device in the chamber discharge operation shown in FIG. 6.

The condition confirmation flow by the controller 2*a* of the blood smear preparation device 2 in the chamber 81 discharge operation in the present embodiment is described below with reference to FIG. 10. First, in step S31, the CPU 50*a* of the blood smear preparation device 2 determines whether or not the chamber 81 staining solution discharge operation has ended; and when it has been determined that the chamber 81 staining solution discharge operation has ended, the routine advances to step S32. Thereafter, in step S32, the CPU 50a measures the time required from the start of the chamber 81 staining solution discharge operation until the discharge operation ends when the float switch 81b is turned OFF, and determines whether or not the chamber 81 discharge operation has ended by whether the float switch 81b has been turned OFF within 2 seconds. When the CPU 50a has determined that the chamber 81 discharge operation has ended when the float switch 81b is turned OFF within 2 seconds in step S32, then in step S33, the CPU 50a determines that the chamber 81 discharge operation is a normal condition, and the routine advances to step S39. When the CPU 50a has determined that the chamber 81 discharge operation has not ended and the float switch 81b has not been turned OFF within 2 seconds in step S32, then in step S34, the CPU 50a determines whether or not the chamber 81 discharge operation has ended and the float switch 81b has turned OFF within 5 seconds. When the CPU 50a has determined that the chamber 81 discharge operation has ended when the float switch 81b is turned OFF within 5 seconds in step S34, then in step S35, a chamber 81 discharge operation warning condition is confirmed, and an error code is called from the error code table and saved as an error log in the RAM 50c (refer to FIG. 16) of the blood smear preparation device 2. Thereafter, the routine advances to step S39. The error code table allocates error codes to various warning conditions and is prepared beforehand, and is saved in the ROM 50b of the blood smear preparation device 2.

In step S36, the CPU 50a of the blood smear preparation device 2 transmits the warning information from the blood smear preparation device 2 to the personal computer 4. When the CPU 50a has determined that the chamber 81 discharge operation has not ended and the float switch 81b has not turned OFF within 5 seconds in step S34, then in step S37, the controller 2a of the blood smear preparation device 2 confirms that the chamber 81 discharge operation is an abnormal (error) condition, and an error code is called from the error code table and saved as an error log in the RAM 50c (refer to FIG. 16) of the blood smear preparation device 2. The error code table allocates error codes to various abnormal conditions and is prepared beforehand, and saved in the ROM 50c of the blood smear preparation device 2. Then, in step S38, the CPU 50a displays an error display on the display operation unit 2b of the blood smear preparation device 2, and transmits error information to the personal computer 4, whereupon the routine advances to step S39. In step S39, the CPU 50a determines whether or not to begin shutdown. When the CPU 50a determines in step S39 to not begin shutdown, the routine returns to step S31. When the CPU 50a determines to start shutdown in step S39, then in step S40 shutdown start information is transmitted to the personal computer 4, the blood smear preparation device 2 shuts down and the process ends. In this way the controller 2a of the blood smear preparation device 2 is able to confirm the condition in the chamber 81 discharge operation.

The flow of the information transmission operation performed by the controller 4a of the personal computer 4 in the present embodiment is described below with reference to FIG. 11. First, in step S101, the CPU 61a of the personal computer 4 determines whether or not warning information or error information has been received from the blood smear preparation device 2. When the CPU 61a determines in step S101 that warning information or error information has been received, the routine advances to step S102. Thereafter, in step S102, the warning information and error information are saved on the hard disk 61d (refer to FIG. 17), and the routine advances to step S103. When the CPU 61a determines in step S101 that warning information or error information has not been received, the routine advances to step S103. In step S103 the CPU 61a determines whether or not shutdown start information has been received from the blood smear preparation device 2. When the CPU 61a determines in step S103 that shutdown start information has not been received, the routine returns to step S101. When the CPU 61a determines in step S103 that shutdown start information has been received, then in step S104 the warning information and error information are transmitted to the maintenance management device 5 by electronic mail, and the process ends. In this way the controller 4a of the personal computer 4 is able to transmit information received from the blood smear preparation device 2 to the maintenance management device 5 installed off-site at a maintenance company.

Thereafter, the cassette 23 containing the smeared slide glass 10 is sequentially fed from the conveyor belt 27b to the conveyor belt 28a of the storage unit 28. Then, the cassette 23 is transported by the conveyor belt 28a and stored in the storage unit 28.

Figures 13, 14:
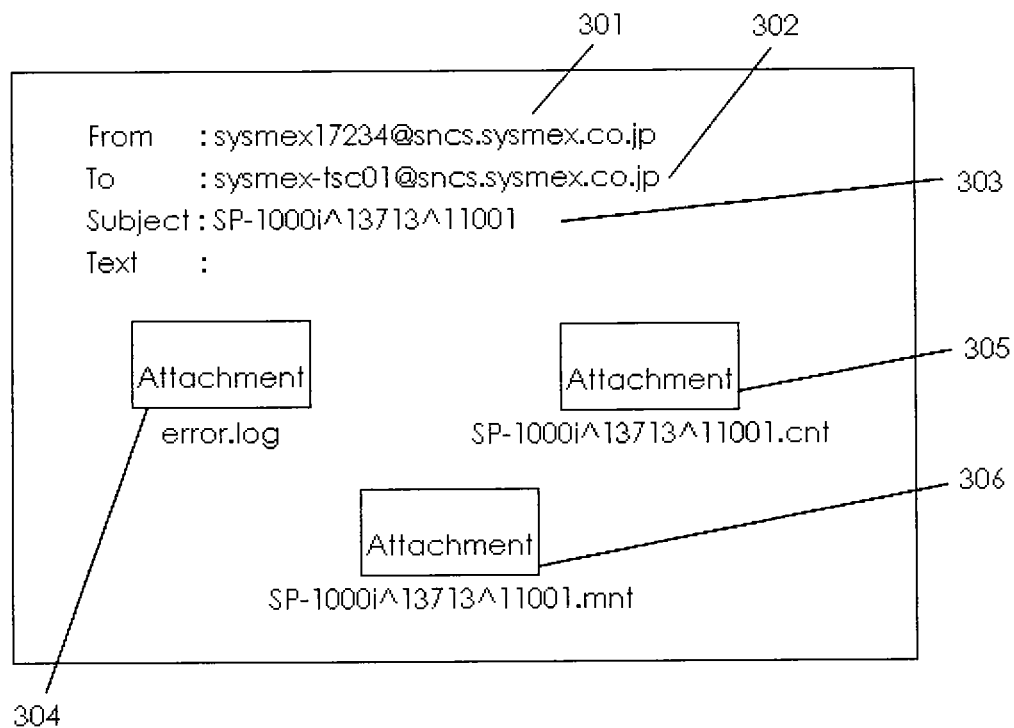
FIG. 13 is a table showing the content of an error log.
FIG. 14 shows the content of an electronic mail with the attached error log of FIG. 12.

The error log saved in the RAM 50c of the blood smear preparation device 2 is described below. A table illustrating an error log is shown in FIG. 13. As shown in FIG. 13, the error log includes a serial number 201, device ID number 202, error generation date 203, error generation time 204, and error code 205. The 22511 of the error code 205 is a code corresponding to a warning condition in the raising operation of the dispensing pipette 21b, and the 141001 of the error code 205 is a code corresponding to an abnormal condition of the discharge operation of the chamber 81. The error log is transmitted to the personal computer 4 and saved to the hard disk 61d. The error log saved on the hard disk 61d is transmitted to the maintenance management device 5 by electronic mail by the CPU50a of the personal computer 4.

The format of the electronic mail transmitted to the maintenance management device 5 is shown in FIG. 14. As shown in FIG. 14, the electronic mail includes a transmission origin address 301, transmission destination address 302, subject header 303, error log attachment file 304, operation count attachment file 305, and maintenance part and replacement part log attachment file 306.

The CPU 71a of the maintenance management device 5, which has received the electronic mail with the error log attachment file, classifies the information contained in the error log for each error code, and calculates the frequency of occurrence of each error code. The CPU 71a classifies the condition of the blood smear preparation device 2 as warning condition and abnormal condition based on the calculated results.

If a warning condition occurs more than a stipulated number of times, the CPU 71a a message indicating that the warning condition has occurred more than the stipulated number of times is displayed on the display 72 to alert the personnel of the maintenance company. The personnel who receives this message contacts the institution where the blood smear preparation device 2 is located, or discusses the circumstances with maintenance supervisors to devise countermeasures. A maintenance employee is dispatched to the concerned institution as necessary, and performs the required repairs and maintenance on the parts of the device associated with the warning condition.

The CPU 71a of the maintenance management device 5 also may compares a occurrence count of the warning condition with a predetermined standard number occurrence, determines the requirements of repairs and maintenance on the parts of the device associated with the warning condition, and displays a message of the determined result on the display unit 72.

In the case of an abnormal condition, the CPU 71a of the maintenance management device 5 displays a message indicating abnormal condition on the display unit 72 to alert the personnel of the maintenance company. The personnel who receives this message contacts the institution where the blood smear preparation device 2 is located, and dispatches a maintenance supervisor to the concerned institution to perform the required repairs and maintenance on the parts of the device associated with the abnormal condition.

The CPU 71a of the maintenance management device 5 also may transmit the notification of warning condition or abnormal condition of the blood smear preparation device 2 to the portable terminal of a maintenance employee.

In the present embodiment described above, the controller 2a of the blood smear preparation device 2 is provided to compare the number of pulses of the raise-lower drive motor 21g necessary from the start to the end of the raising operation of the dispensing pipette 21b of the blood smear preparation device 2, a standard number of pulses of the raise-lower drive motor 21g within a non-abnormal condition range of the raising operation of the dispensing pipette 21b of the blood smear preparation device 2 (2700 and 3300: first threshold), and a standard number of pulses of the raise-lower drive motor 21g for determining an abnormal condition of the raising operation of the dispensing pipette 21b of the blood smear preparation device 2 (2400 and 3600: second threshold), such that the controller 2a is capable of easily determining a warning condition in which there is a high possibility of future damage compared to the normal condition of the raising operation of the dispensing pipette 21b of the blood smear preparation device 2. Furthermore, the controller 4a of the personal computer 4 is provided to transmit over a network the warning information representing the warning condition of a high possibility of future damage compared to the normal condition in the raising operation of the dispensing pipette 21b of the blood smear preparation device 2 to the maintenance management device (server) 5 installed off site, such that the maintenance company at which the maintenance management device (server) 5 is installed can easily confirm the warning condition of the raising operation of the dispensing pipette 21b of the blood smear preparation device 2. In this way, the problem can be dealt with before a breakdown occurs in the clinical specimen processing apparatus 1 since suitable maintenance can be performed at the stage before a breakdown occurs in the clinical specimen processing apparatus 1 which includes the blood smear preparation device 2. As a result, since the number of breakdowns is reduced in the clinical specimen processing apparatus 1, there is a reduction in the number of times the clinical specimen processing apparatus 1 is shutdown due to abnormality (breakdown) of the blood smear preparation device 2.

In the above embodiment, the controller 2a of the smear specimen preparation device 2 is provided to compare the signals (time and pulse number) detecting the operations and the respective first threshold value and second threshold value in the suction operation and discharge operation of the chamber 81, and the retraction operation of the dispensing pipette 21b in the same manner as the raising operation of the dispensing pipette 21b described above, such that the controller 2a can easily determine a warning condition which has a high possibility of future breakdown compared to the normal condition in the suction operation and discharge operation of the chamber 81 and the retraction operation of the dispensing pipette 21b, and the maintenance company at which the maintenance management device (server) 5 is installed can easily, by means of the controller 4a of the personal computer 4, confirm the warning condition of the suction operation and discharge operation of the chamber 81 and the retraction operation of the dispensing pipette 21b of the blood smear preparation device 2.

Furthermore, although a notification of the warning condition of the blood smear preparation device 2 is transmitted to the maintenance management device (server) 5 in the aforesaid embodiment, a warning condition having a high possibility of future breakdown also may be displayed on the operation display unit 2b of the blood smear preparation device 2 when the warning condition has occurred a standard number of times.

In the above embodiment, the blood smear preparation device 2 receives notification of a warning condition or an abnormal condition from the maintenance management device 5, and the maintenance personnel of the maintenance company contact the institution which owns the blood smear preparation device 2 with the warning condition or abnormal condition, however, a message indicating required maintenance or parts replacement of the target blood specimen preparation device 2 which has the warning condition or abnormal condition also may be transmitted from the maintenance management device 5 to the to the personal computer 4 connected to the blood smear preparation device 2, and furthermore the controller 4a of the personal computer 4 may transmit this message to the controller 2a of the blood smear preparation device 2, and the controller 2a of the blood smear preparation device 2 which receives this message may display the message on the operation display unit 2b. Moreover, this message also may be displayed on the display unit 62 of the personal computer 4. In addition, the controller 2a of the blood smear preparation device 2 may also display a message indicating the need for maintenance and parts replacement of the associated part corresponding to the warning condition or abnormal condition on the operation display unit 2b. In this way it is possible to inform a user of the need for parts replacement before the part is actually replaced, and the usage schedule of the blood smear preparation device 2 can be reevaluated by displaying a message indicating the need of parts replacement on the display unit 62 of the personal computer 4 or the operation display unit 2b of the blood smear preparation device 2.

The embodiment of the present disclosure is an example in all respects and is not to be considered as limiting in any way. The scope of the present invention is expressed in the claims and not in the description of the embodiments, and further includes all modifications within the scope of the claims and equivalent meanings appertaining thereto.

Although the present invention is described by way of example in terms of a clinical specimen processing apparatus including a blood smear preparation device in the above embodiment, the invention is not limited to this arrangement and is further applicable to other clinical specimen processing apparatuses. For example, the present invention is also applicable to clinical specimen processing apparatuses such as blood corpuscle analyzers (blood analyzers) which analyze the number of blood corpuscles, hematocrit, hemoglobin and the like; immunoassay devices for determining infectious disease, cancer marker antigens or antigen concentration; blood coagulation measuring devices for determining coagulation function of serum and plasma samples; biochemical analyzers for measuring serum total protein, and enzyme activity as an organ function indicator; urine qualitative analysis device for determining urine protein, sugar, and presence/absence of red blood cells in urine samples; or urine sediment analyzers for quantifying red blood cells, white blood cells, epithelial cells, cast and bacteria.

Although the example of the present embodiment describes transmitting condition information (warning information and error information) of the blood smear preparation device from a personal computer to a maintenance management device at shutdown of the blood smear preparation device, the present invention is not limited to this arrangement inasmuch as the condition information (warning information and error information) of the blood smear preparation device also may be transmitted from a personal computer to a maintenance management device at startup of the blood smear preparation device start. Furthermore, information requiring urgent attention among the error information and warning information also may be transmitted from a personal computer to a maintenance management device in real time without waiting for shutdown or startup.

Figure 11:
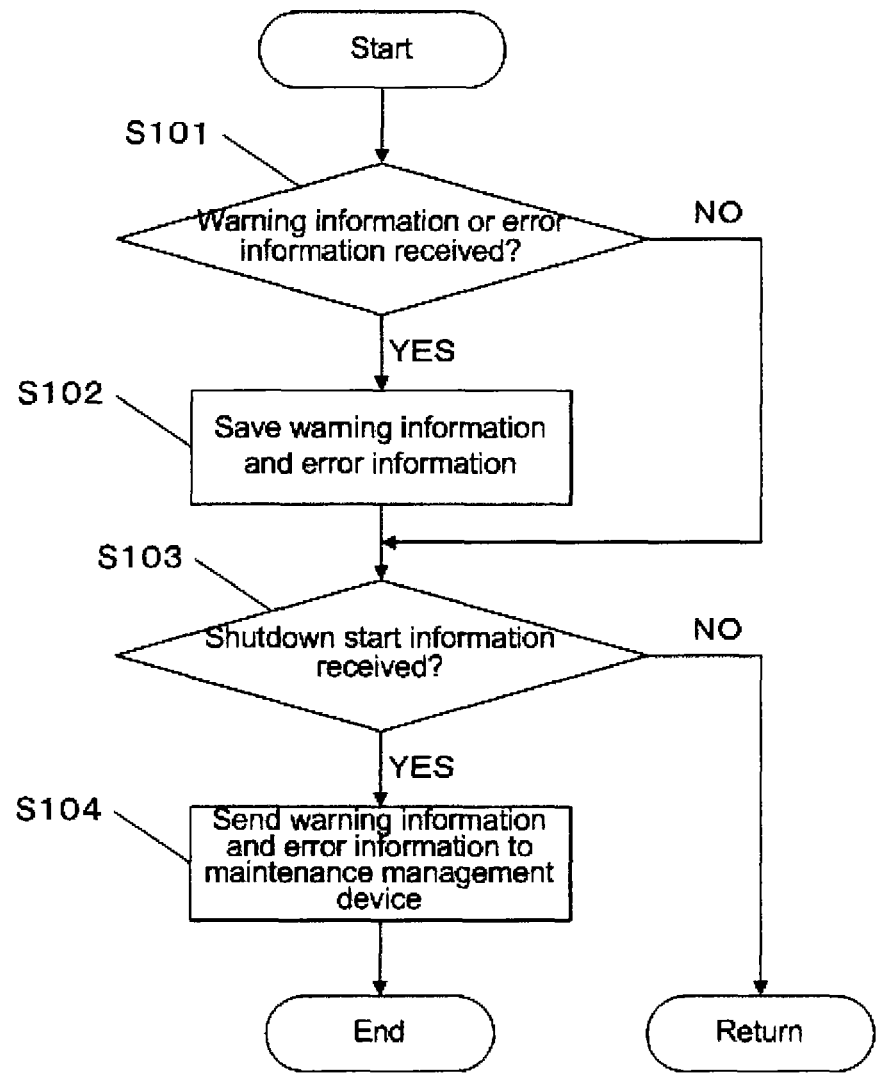
FIG. 11 is a flow chart illustrating the information transmission operation performed by the controller of the personal computer shown in FIG. 1.
Figure 12:
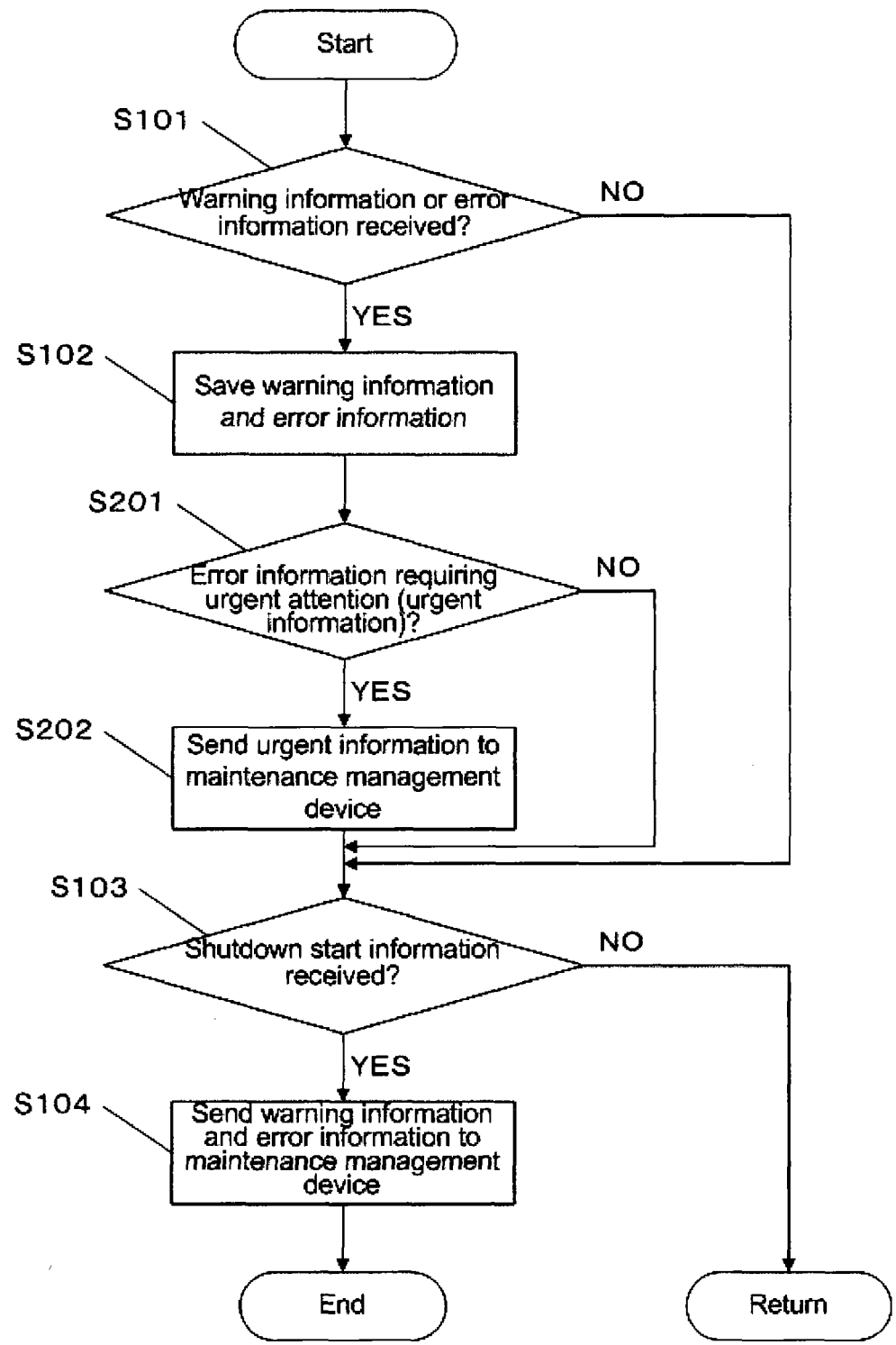
FIG. 12 is a flow chart illustrating the information transmission operation performed by the controller of the personal computer in a modification of the embodiment of the present invention shown in FIG. 11.

For example, FIG. 12 is a flow chart illustrating the information transmission operation by the controller 4a of the personal computer 4 in a modification of the embodiment of the present invention shown in FIG. 11. Referring to FIG. 12, in this modification condition conformation flow error information in each operation described in the flow chart of FIGS. 7 through 10 is transmitted in real time from the personal computer 4 to the maintenance management device (server) 5 without waiting for the shutdown of the blood smear preparation device 2. That is, in steps S101 through S102 shown in FIG. 12, after processing identical to that of steps S101 through S102 of FIG. 11 is executed, then in step S102 the CPU 61a of the personal computer 4 determines whether or not the error information saved on the hard disk 61d of the personal computer 4 is error information requiring urgent attention (urgent information). Then, in step S201, when the CPU 61a has determined that the error information is urgent information, then in step S202 the urgent information is transmitted by means of electronic email immediately to the maintenance management device 5 without waiting for shutdown. When the urgent information is transmitted by electronic mail to the maintenance management device 5, the controller 2a of the blood smear preparation device 2 halts subsequent operation of the blood smear preparation device 2. Then, in step S201, when the CPU 61a has determined that the error information is not urgent information, then the routine advances to step S103, and the subsequent processes of step S 103 and thereafter are performed as shown in FIG. 11.

The urgent information of the blood smear preparation device 2 is embedded within the text body of the electronic mail without preparing a file attachment, and transmitted to the maintenance management device 5. For example, the device ID, date, time, error code and lie information are included in the text body of the electronic mail in this case.

Figure 15:
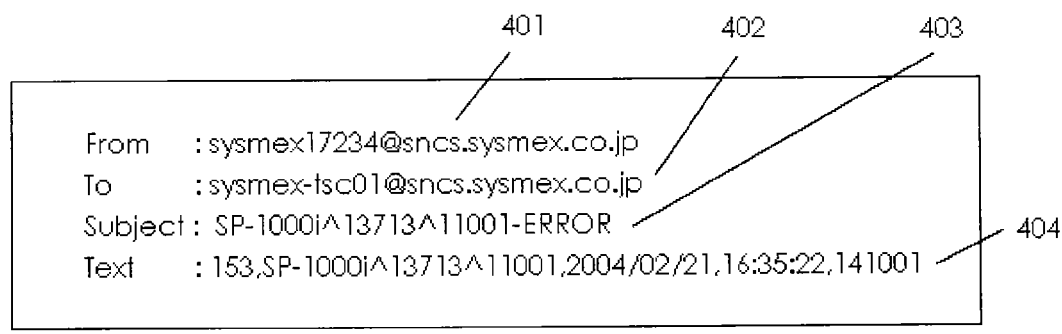
FIG. 15 is a structural diagram showing the content of an electronic mail, which includes urgent information of the blood smear preparation device.

The specific format of the electronic mail (urgent error mail) containing the urgent information is shown in FIG. 15. The urgent error mail shown in FIG. 15 includes the transmission original mail address 401, transmission destination mail address 402, subject header 403, and text body 404. The subject header 403 ads the text "ERROR" to the device ID, so that a reader knows at a glance that it is urgent information. Furthermore, The text body 405 includes a serial number (153), device ID (SP-1000iˆ13713ˆ11001), error generation date (2004/02/21), error generation time (16:35:22), error code (141001). The error code 141001 indicates an abnormal condition in the discharge operation of the chamber 81 of the blood smear preparation device 2.

The CPU 71a of the maintenance management device 5 which received the urgent error mail displays the a message indicating the urgent abnormal condition of the blood smear preparation device 2 on the display unit 72 to alert the personnel of the maintenance company. The personnel who receives this message contacts the institution where the blood smear preparation device 2 with the urgent abnormal condition is located, and dispatches a maintenance supervisor to the concerned institution to perform the parts replacement of the parts of the device associated with the abnormal condition. The CPU 71a of the maintenance management device 5 also may transmit the notification of the abnormal condition of the blood smear preparation device 2 to the portable terminal of a maintenance employee.

Although electronic mail is used in the aforesaid embodiment to transmit condition information (warning information and error information) of the blood smear preparation device to a maintenance management device (server), the present invention is not limited to this arrangement inasmuch as the condition information (warning information and error information) of the blood smear preparation device also may be transmitted to a maintenance management device (server) by data communication methods other than electronic mail.

Although the example in the above embodiment describes the controller 4a of the personal computer 4 as having an electronic mail transmission function, the present invention is not limited to this arrangement inasmuch as the controller 2a of the blood smear preparation device 2 also may have an electronic mail transmission function. In this case, the clinical specimen processing apparatus 1 does not require the personal computer 4, and the structure of the clinical specimen processing apparatus 1 may be simplified.

In the example described in the above embodiment, the warning information of the raising operation and retraction operation of the dispensing pipette 21b of the suction and dispensing mechanism 21 of the blood smear preparation device 2, and the warning information of the suction operation and discharge operation of the chamber 81 which supplies staining solution to the third suction and discharge unit 27d of the staining unit 27 of the blood smear preparation device 2 are transmitted to a maintenance management device, however, the present invention is not limited to this arrangement inasmuch as the warning information of operations of other parts of the blood smear preparation device 2 also may be transmitted to the maintenance management device. For example, warning information of the raising operation of the piano 21a of the suction and dispensing mechanism 21, warning information of the suction operation and discharge operation of the chamber supplying staining solution and rinse water to the suction and discharge units other than the third suction and discharge unit 27d of the staining unit 27, and warning information of the suction operation and discharge operation of the other chambers (for example, waste fluid chamber and the like) of the blood smear preparation device 2 also may be transmitted to the maintenance management device.

Furthermore, in the above embodiment the controller 2a of the blood smear preparation device 2 is provided with a function for determining an abnormal condition of the blood smear preparation device 2, and a function for determining a warning condition having a high possibility of future breakdown compared to the normal condition of the blood smear preparation device 2, however, the controller 4a of the personal computer 4 also may be provided with a function for determining an abnormal condition of the blood smear preparation device 2, and a function for determining a warning condition having a high possibility of future breakdown compared to the normal condition of the blood smear preparation device 2. In this case, the operation information of the blood smear preparation device 2 is transmitted from the controller 2a of the blood smear preparation device 2 to the controller 4a of the personal computer 4, and the controller 4a determines the warning condition and abnormal condition of the blood smear preparation device 2 based on the received operation information. In the above embodiment, the operation information represents the number of pulses of the raise-lower drive motor 21g of the blood smear preparation device 2, number of pulses of the forward-backward drive motor 21d, time required for the float switch 81b to turn ON in the suction operation of the chamber 81, and time required for the float switch 81b to turn OFF in the discharge operation of the chamber 81.

What is claimed is:

1. A clinical specimen processing system including a clinical specimen processing apparatus situated at a user facility and maintenance management device situated in at a maintenance facility located in a building different from the user facility, the clinical specimen processing apparatus comprising:
a liquid transport system including a liquid supply, a pressure regulator, a liquid flow passage and a pressurized chamber coupled to the liquid supply and the pressure regulator, the pressurized chamber including a float switch responsive to a quantity of liquid in the pressurized chamber;
at least one memory that stores programs executable by at least one processor of a computer system within the clinical specimen processing apparatus, wherein, in response to a signal from the float switch, the processor executes the programs to:
activate the pressure regulator to transport liquid from the liquid supply to the pressurized chamber through the liquid flow passage;
deactivate the pressure regulator when the float switch detects that a required amount of liquid has been transported to the pressurized chamber;
measure an amount of time elapsed between a beginning and an end of the liquid transport; and
when detecting that the required amount of liquid has been transported from the liquid supply to the pressurized chamber, diagnose the liquid transport system by:
(a) determining whether the measured elapsed time falls within a first time range, wherein when the measured elapsed time is determined to fall within the first time range, the at least one processor diagnoses the liquid transport system as being in a normal condition;
(b) determining whether the measured elapsed time falls within a second time range, wherein when the measured elapsed time is determined to fall within the second time range, the at least one processor diagnoses the liquid transport system as being in a warning condition, the controller does not display an alert message on the display and stores and transmits warning information to the maintenance management device over a network; and
(c) determining whether the measured elapsed time falls within a third time range, wherein when the measured elapsed time is determined to fall within the third time range, the at least one processor diagnoses the liquid transport system as being in an error condition, the controller displays an alert message on the display and stores and transmits error information to the maintenance management device over the network, the maintenance management device comprising:
a maintenance management device display;
at least one memory that stores an error log and programs executable by a processor of a computer system within the maintenance management device, wherein, in response to receiving the warning information or the error information, the processor executes the programs to:
classify the warning information or the error information in the error log;
calculate the number of times each warning information and error information is received, and
display on the maintenance management device a maintenance alert if the warning information or error information occurs more than a predetermined number of times.

2. The clinical specimen processing system according to claim 1, wherein the clinical specimen processing apparatus comprises a blood analyzer, or a smear specimen preparation device.

3. The clinical specimen processing system according to claim 1, wherein the at least one processor of the clinical specimen processing apparatus transmits the stored warning information to the processor of the maintenance management device when the clinical specimen processing apparatus is being turned off.

4. The clinical specimen processing system according to claim 1, wherein the at least one processor of the clinical specimen processing apparatus evaluates the stored error information to determine whether the error information is urgent information or not and, when the error information is determined to be urgent information, transmits the error information upon determination to the processor of the maintenance management device for immediate maintenance.

5. The clinical specimen processing system according to claim 1, wherein the at least one processor of the clinical specimen processing apparatus transmits the stored error information to the processor of the maintenance management device when the clinical specimen processing apparatus is being turned off.

6. The clinical specimen processing system according to claim 1, wherein the at least one processor of the clinical specimen processing apparatus executes the programs to prepare an electronic mail including the warning information and to transmit the electronic mail to the processor of the maintenance management device.

7. The clinical specimen processing system according to claim 1, wherein the at least one processor of the clinical specimen processing apparatus executes the programs to prepare an electronic mail including the error information and to transmit the electronic mail to the processor of the maintenance management device.

8. The clinical specimen processing system according to claim 4, wherein the at least one processor of the clinical specimen processing apparatus executes the programs to prepare an electronic mail including the urgent information and to transmit the electronic mail to the processor of the maintenance management device.

9. The clinical specimen processing system according to claim 1, wherein the liquid transport system includes a mix chamber and a diaphragm pump, the diaphragm pump suctions the liquid from the pressurized chamber and sends the suctioned liquid to the mix chamber.

* * * * *